US006306663B1

(12) United States Patent
Kenten et al.

(10) Patent No.: US 6,306,663 B1
(45) Date of Patent: Oct. 23, 2001

(54) CONTROLLING PROTEIN LEVELS IN EUCARYOTIC ORGANISMS

(75) Inventors: John H. Kenten, Boyds; Steven F. Roberts, Bethesda, both of MD (US)

(73) Assignee: Proteinex, Inc., Gaithersburg, MD (US)

( * ) Notice: Subject to any disclaimer, the term of this patent is extended or adjusted under 35 U.S.C. 154(b) by 0 days.

(21) Appl. No.: 09/406,781

(22) Filed: Sep. 28, 1999

Related U.S. Application Data
(60) Provisional application No. 60/119,851, filed on Feb. 2, 1999.

(51) Int. Cl.[7] .................................................. G01N 33/566
(52) U.S. Cl. .......................... 436/501; 424/94.1; 435/4; 435/7.72; 435/41; 435/106; 514/2; 530/300; 530/350; 930/20
(58) Field of Search .............................. 435/41, 106, 4, 435/7.72; 436/501; 514/2; 530/300, 350; 930/20; 424/94.1

(56) References Cited

U.S. PATENT DOCUMENTS 5,122,463  6/1992  Varshavsky et al. .
5,766,927  6/1998  Baker et al. .

OTHER PUBLICATIONS

Varshavsky A. The N–end rule: functions, mysteries and uses. Proceeding of the National Academy of Sciences (1996) vol. 93, pp. 12142–12149.*

Briesewitz, Robert, et al, "Affinity modulation of small-molecule ligands by borrowing endogenous protein surfaces," *Proc. Natl. Acad. Sci. USA*, vol. 96, pp. 1953–1958, Mar. 1999.

Kwon, Yong Tae, et al, "Bivalent Inhibitor of the N–end Rule Pathway," *The Journal of Biological Chemistry*, vol. 274, No. 25, pp. 18135–198139, Jun. 18, 1999.

Solomon, Vered, et al, "The N–end Rule Pathway Catalyzes a major Fraction of the Protein Degradation in Skeletal Muscle," *The Journal of Biological Chemistry*, vol. 273, No. 39, pp. 25216–25222, Sep. 25, 1998.

Yewdell, J., et al, "Generating MHC class I ligands from viral gene products," *Immunological Review*, vol. 172, Dec. 1999 (Abstract only).

Souroujon, M.C., et al, "Peptide modulators of protein—protein interactions in intracellular signaling," *Nature Biotechnology*, vol. 16, No. 10, 1998 (Abstract only).

Liu, Jun O., "Recruitment of proteins to modulate protein—protein interactions," *Chemical Biology*, vol. 6, No. 8, pp. 213–215, Aug. 1999.

Fassina, G., "Complementary peptides as antibody mimetics for protein purification and assay," *Immunomethods*, vol. 5, No. 2, 1994 (Abstract only).

* cited by examiner

*Primary Examiner*—Jeffrey Stucker
*Assistant Examiner*—Ulrike Winkler
(74) *Attorney, Agent, or Firm*—Nixon & Vanderhye

(57) ABSTRACT

The invention relates to novel compounds comprising a ubiquitination recognition element and a protein binding element. The invention also relates to the use of said compounds for modulating the level and/or activity of a target protein. The compounds are useful for the treatment of disease such as infections, inflammatory conditions, cancer and genetic diseases. The compounds are also useful as insecticides and herbicides.

1 Claim, 7 Drawing Sheets

Scheme 1 Synthesis of L-chicoric acid

Scheme 2   Synthesis of N-bromoacetyl ethylenediamine

Scheme 3  Synthesis of bromoacetylated derivative of L-chicoric acid

Scheme 4 Conjugation of recognition/linker to bromoacetylated L-chicoric acid

CONTROLLING PROTEIN LEVELS IN EUCARYOTIC ORGANISMS

This application claims priority to the provisional Application No. 60/119,851, filed Feb. 2, 1999.

FIELD OF INVENTION

The subject invention relates to novel compounds and their use in controlling levels of proteins in eukaryotic organisms.

BACKGROUND OF INVENTION

Ubiquitin Mediated Protein Degradation

Ubiquitin is known to be one of several factors required for ATP-dependent protein degradation in eukaryotic cells. One function of intracellular protein degradation, most of which is ATP-dependent, is selective elimination of damaged and otherwise abnormal proteins. Another is to confer short half-lives on undamaged proteins whose concentrations in the cell must vary as functions of time, as is the case, for example, with many regulatory proteins. Many other proteins, while long-lived as components of larger macromolecular complexes such as ribosomes and oligomeric proteins, are metabolically unstable in a free, unassociated state. Ubiquitination is also involved in the control of cell surface receptors such as platelet-derived growth factor (PDGF), the T cell receptor, G protein-coupled receptors and others. In addition to these proteins complexed with ubiquitin, ubiquitin is also found covalently linked to lipids in membranes (Guarino, L A, 1995, Cell 80, 301–309).

Ubiquitin, a 76-residue protein, is present in eukaryotes either free or covalently joined, through its carboxyl-terminal glycine residue, to various cytoplasmic, nuclear, and integral membrane proteins. A family of ubiquitin-conjugating enzymes (also called E2 enzymes) catalyzes the coupling of ubiquitin to such proteins (ubiquitination) generally in combination with a recognition element called E3 that may also function to carry out the ubiquitination. The fact that the protein of ubiquitin is conserved among eukaryotes to an extent unparalleled among known proteins suggests that ubiquitin mediates a basic cellular function.

It has been shown that selective degradation of many short-lived proteins requires a preliminary step of ubiquitin conjugation to a targeted proteolytic substrate. One role of ubiquitin is to serve as a signal for attack by proteases specific for ubiquitin-protein conjugates (Finley and Varshavsky, Trends Biochem. Sci. 10:343–348 (1985)).

At least some short-lived proteins are recognized as such because they contain sequences (degradation signals) which make these proteins substrates of specific proteolytic pathways. The first degradation signal to be understood in some detail comprises two distinct determinants: the protein's amino-terminal residue and a specific internal lysine residue, the N-end rule (Bachmair et al., Science 234:179–186 (1986); Bachmair and Varshavsky, Cell 56:1013–1032 (1989)). The N-end rule, a code that relates the protein's metabolic stability to the identity of its amino-terminal residue (Bachmair et al., Science 234:179–186 (1986), is universal in that different versions of the N-end rule operate in all of the eukaryotic organisms examined, from yeast to mammals (Gonda et al., J. Biol. Chem. 264:16700–16712 (1989)).

The second essential determinant of the N-end rule-based degradation signal, referred to as the second determinant, is a specific internal lysine residue in the substrate protein that serves as the site of attachment of a multiubiquitin chain. Formation of the multiubiquitin chain on a targeted short-lived protein is essential for the protein's subsequent degradation. The enzymatic conjugation of ubiquitin to other proteins involves formation of an isopeptide bond between the carboxy-terminal glycine residue of ubiquitin and the epsilon-amino group of a lysine residue in an acceptor protein. In a multiubiquitin chain, ubiquitin itself serves as an acceptor, with several ubiquitin moieties attached sequentially to an initial acceptor protein to form a chain of branched ubiquitin-ubiquitin conjugates (Chau et al., Science 243:1576–1583 (1989)).

The elucidation of the fundamental rules governing the metabolic stability of proteins in cells, and especially the deciphering of the N-end rule-based degradation signal, has made possible the manipulation of proteins to vary their half-lives in vivo (Bachmair and Varshavsky, Cell 56:1019–1032 (1989)).

The N-degron is an intracellular degradation signal whose essential determinant is a specific ("destabilizing") N-terminal amino acid residue of a substrate protein. A set of N-degrons containing different destabilizing residues is manifested as the N-end rule, which relates the in vivo half-life of a protein to the identity of its N-terminal residue. The fundamental principles of the N-end rule, and the proteolytic pathway that implements it, are well established in the literature (see, e.g., Bachmair et al., Science 234: 179 (1986); Varshavsky, Cell 69: 725 (1992), U.S. Pat. Nos.: 5,122,463; 5,132,213; 5,093,242 and 5,196,321) the disclosures of which are incorporated herein by reference in their entirety.

In eukaryotes, the N-degron comprises at least two determinants: a destabilizing N-terminal residue and a specific internal lysine residue (or residues). The latter is the site of attachment of a multiubiquitin chain, whose formation is required for the degradation of at least some N-end rule substrates. Ubiquitin is a protein whose covalent conjugation to other proteins plays a role in a number of cellular processes, primarily through routes that involve protein degradation.

In a stochastic view of the N-degron, each internal lysine of a protein bearing a destabilizing N-terminal residue can be assigned a probability of being utilized as a multiubiquitination site, depending on time-averaged spatial location, orientation and mobility of the lysine. For some, and often for all of the Lys residues in a potential N-end rule substrate, this probability is infinitesimal because of the lysine's lack of mobility and/or its distance from a destabilizing N-terminal residue.

It is possible to construct a thermolabile protein bearing a destabilizing N-terminal residue in such a way that the protein becomes a substrate of the N-end rule pathway only at a temperature high enough to result in at least partial unfolding of the protein. This unfolding activates a previously cryptic N-degron in the protein by increasing exposure of its (destabilizing) N-terminal residue, by increasing mobilities of its internal Lys residues, or because of both effects at once. Since proteolysis by the N-end rule pathway is highly processive, any protein of interest can be made short-lived at a high (nonpermissive) but not at a low (permissive) temperature by expressing it as a fusion to the thus engineered thermolabile protein, with the latter serving as a portable, heat-inducible N-degron module.

The heat-inducible N-degron module can be any protein or peptide bearing a destabilizing N-terminal residue that becomes a substrate of the N-end rule pathway only at a temperature high enough to be useful as a nonpermissive temperature.

The idea of metabolically destabilizing a protein or peptide of interest using a protein or peptide (ie targeting a protein or peptide for degradation) has been described in U.S. Pat. No. 5,122,463. This metabolic destabilization requires that the protein or peptide of interest must contain a second determinant of the N-end rule-based degradation signal. The method comprises contacting the protein or peptide of interest with a targeting protein or peptide that interacts specifically with the protein or peptide of interest. The targeting peptide or protein is characterized as having a destabilizing amino-terminal amino acid according to the N-end rule of protein degradation.

The ability to activate the ubiquitination and degradation of other proteins not containing an N-terminus N-degron signal has been shown in a multisubunit protein where the N-degron signals are located on different subunits and still target a protein for destruction (U.S. Pat. No. 5,122,463). Moreover, in this case (trans recognition) only the subunit that bears the second N-degron signal (lysine) determinant is actually degraded. Thus, an oligomeric protein can contain both short-lived and long-lived subunits. In these examples the demonstrations are all based on known multisubunit proteins and alterations of these to bring about the destabilization of subunits involved in these multisubunit complexes.

A different aspect of targeting the ubiquitination system based on chimeric proteins of E2 to achieve selective targeting and alterations in the levels of proteins has been described (Gosink M M and Vierstra R D, 1995, Proc. Natl. Acad. Sci. 92, 9117–9121). These researchers demonstrated that selective ubiquitination and degradation can be achieved using a protein, which is a fusion protein of a ubiquitinating protein with a binding protein.

In one interesting study of the N end rule, the degradation of DHFR was stabilized by the binding of a small molecule indicating that binding small molecules could prevent the degradation of proteins. This was also suggested in U.S. Pat. No. 5,122,463 where the idea of using peptides and proteins to target the ubiquitination of proteins to which they bind is suggested. In this patent the peptides are described as binding in such a way that the peptide interferes with the folding of the target protein "folding-interfering targeting peptides" suggesting also that peptides binding might prevent degradation as seen with DHFR. Indeed in this patent the focus for the peptides is the sequence of the target protein to give rise to these destabilizing residues.

Other Protein Covalent Modification for Protein Targeting

A number of systems mirror the protein modification pathway of ubiquitin. Among these are based on the attachment of Apg12, Rub1/Nedd8 and Smt3/SUMO-1 to proteins in addition to the ubiquitin pathway. In these systems homology at the level of sequence is seen but also clear parallels can be drawn based on the functional elements involved in the various systems (S Jentsch and H. D. Ulrich, Nature (1998) 395, 321–322).

In the case of the Apg12 system this protein is involved in the autophagy of various cellular components. Apg12 appears to be the functional homologue of ubiquitin and is transferred via Apg7 and Apg10 the functional homologue of the E1 and E2 ubiquitin conjugating enzymes, respectively. Apg12 transferred via Apg7 and Apg10 is used to modify Apg5 to activate autophagy. The analysis of the sequence of Apg7 shows a considerable homology to the E1 enzymes of the ubiquitin pathway. In the case of Rub1/Nedd8 system this protein is involved in some regulatory role. The Smt3/SUMO-1 system is involved in the targeting of proteins.

Drug Targets

The number of drug targets for human therapeutics is around 400 human gene products, such as enzymes, receptors and ion channels. But there may be 2500–5000 molecular targets whose exploitation may be capable of restoring function in the 100 or so common human polygenic diseases. Many of these new targets are being discovered by the intensive search of the human genome by various groups using focused and random methods.

The following are examples of drug targets which are the subject of investigation by various pharmaceutical companies: B7.1 and B7, TNFR1m(p55), TNFR2 (p75), NADPH oxidase, Bc1/Bax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G proteins ie Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAK/STAT, RXR and similar, HIV 1 protease, HIV 1 integrase, influenza, neuraminidase, hepatitis B reverse transcriptase, sodium channel, multi drug resistance (MDR), protein P-glycoprotein (and MRP), tyrosine kinases, CD23, tyrosine kinase p56 1ck, CD4, CD5, IL-2 receptor, IL-1 receptor, TNF-alphaR, ICAM1, Ca++ channels, VCAM, VLA-4 integrin, selectins, CD40/CD40L, neurokinins and receptors, inosine monophosphate dehydrogenase, p38 MAP Kinase, Ras/Raf/MEK/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-1), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin II, glycine receptor, noradrenaline reuptake receptor, endothelin receptors, neuropeptide Y and receptor, adenosine receptors, adenosine kinase and AMP deaminase, purinergic receptors (P2Y1, P2Y2, P2Y4, P2Y6, P2X1–7), farnesyltransferases, geranylgeranyl transferase, TrkA a receptor for NGF, beta-amyloid, tyrosine kinase Flk-1/KDR, vitronectin receptor, integrin receptor, Her-2/neu, telomerase inhibition, cytosolic phospholipase A2, EGF receptor tyrosine kinase.

Insecticide target examples include, ecdysone 20-monooxygenase, ion channel of the GABA gated chloride channel, acetylcholinesterase, voltage-sensitive sodium channel protein, calcium release channel, and chloride channels.

Herbicide target examples include Acetyl-CoA carboxylase, adenylosuccinate synthetase, protoporphyrinogen oxidase, and enolpyruvylshikimate-phosphate synthase.

These various targets are typically used in screens that look for a compound to alter the level of activity of the selected target and require the compound to be in solution. In some cases the assay to determine activity in a potential compound has to be based on a cell based assay. The best assays for compound screens are where the interaction of two molecules is modulated allowing the development of rapid assays based on the determination of binding.

In addition to the drawbacks of current drug and compound discovery efforts described above, problems of specificity arise due to the common basis for the activity of various compounds. For example in trying to find compounds which block the dopamine receptor, one is interested in the inhibition of a specific receptor sub-type due to its expression in a selected tissue. The binding site of the receptor is designed to bind to dopamine and thus has a common structure across the various sub-types of receptors. This homology of structure at the target site of the discovery effort makes it difficult to identify compounds with optimal levels of specificity for given sub-types and thus difficult to achieve the levels of therapeutic affect desired.

The present invention provides a solution to this problem.

Antigen Presentation

The target degradation of various proteins in the cell is a mechanism for the presentation of various peptides in the context of MHC. It has been demonstrated that the ubiquitination of intracellular proteins leads to the degradation of the protein via the 26S proteasome and enhanced presentation of the resultant peptides in the context of MHC I. This enhanced presentation leads to improved immune responses by the stimulation of various cells involved in the immune system. In many diseases the antigenicity of various proteins does not appear to be potent enough to generate a robust immune response. For example in the case of cancer certain antigens are present but fail to elicite a potent immune response (Tobery T and Siliciano R F., 1999, J Immunol. 162, 639–642). The present invention provides a solution to this problem of generating an improved immune response.

Antisense

Antisense technology is a novel drug therapy approach. Antisense drugs work at the genetic level to interrupt the process by which disease causing proteins are produced. Proteins play a central role in virtually every aspect of human metabolism. Many human diseases are the result of inappropriate protein production. Antisense drugs are designed to inhibit the production of disease causing proteins. These antisense drugs function by binding to specific nucleic acid sequences in a cell and block the production of specific proteins in this way a specific proteins level is reduced. Examples of targets for this technology are virus-based diseases, cancer, Crohn's disease, renal transplant rejection, psoriasis, ulcerative colitis, and inflammation. The specific targets are; HPV, HIV, CMV, hepatitis C, ICAM-1, PKC-alpha, c-raf kinase, Ha-ras, TNF-alpha and VLA-4.

SUMMARY OF INVENTION

The invention comprises compositions and methods for controlling the levels of proteins in eukaryotic organisms. This control of protein levels is achieved using an exogenous molecule able to affect ubiquitination of a given protein. The ubiquitinated protein is targeted for intracellular degradation via normal cellular pathways. The exogenous molecule able to selectively target ubiquitination of a pre-selected protein comprise; a ubiquitination recognition element and target protein binding element for a pre-selected protein covalently linked to form the compositions of the invention.

The ubiquitination recognition element is designed to interact with the ubiquitination mechanisms of the cell allowing their recruitment. The target protein binding element binds to pre-selected protein in order to effectively present the ubiquitin recognition element.

This invention offers a number of improvements over the art especially for drug development. The invention provides a more cost effective route for drug development and drugs with improved activity.

The invention comprises compounds for activating the ubiquitination of a target protein comprising, a ubiquitination recognition element which is able to bind to either the E3 or E2 functional elements of the ubiquitination system, the ubiquitination recognition element has a molecular weight less than 30,000 and has a binding affinity for the E3 and/or E2 elements of the ubiquitination system of at least $10^2$ $M^{-1}$ and; a target protein binding element that is able to bind specifically to a target protein, the target protein binding element has a molecular weight of less than 30,000 and has a binding affinity for the target protein greater than $10^5$ $M^{-1}$, the ubiquitination recognition element is covalently linked to the target protein binding element.

The invention also comprises compounds for activating the ubiquitination of a target protein comprising, a ubiquitination recognition peptide element which is able to bind to either the E3 or E2 functional elements of the ubiquitination system, the ubiquitination recognition peptide element has a molecular weight less than 30,000 and has a binding affinity for the E3 and/or E2 elements of the ubiquitination system of at least $10^2$ $M^{-1}$ and a target protein binding element that is able to bind specifically to a target protein, the target protein binding element has a molecular weight of less than 30,000 and has a binding affinity for the target protein greater than $10^5$ $M^{-1}$, the ubiquitination recognition peptide element is covalently linked to the target protein binding element.

The invention also comprises compounds for activating the ubiquitination of a target protein comprising, a ubiquitination recognition element which is able to bind to either the E3 or E2 functional elements of the ubiquitination system, the ubiquitination recognition element has a molecular weight less than 30,000 and has a binding affinity for the E3 and/or E2 elements of the ubiquitination system of at least $10^2$ $M^{-1}$ and a target protein binding peptide element that is able to bind specifically to a target protein wherein the target protein peptide binding element has a molecular weight of less than 30,000 and has a binding affinity for the target protein greater than $10^5$ $M^{-1}$, wherein the ubiquitination recognition element is covalently linked to the target protein binding peptide element.

The invention comprises compounds for activating the ubiquitination of a target protein comprising, a ubiquitination recognition peptide element which is able to bind to either the E3 or E2 functional elements of the ubiquitination system, wherein the ubiquitination recognition peptide element has a molecular weight less than 30,000 and has a binding affinity for the E3 and/or E2 elements of the ubiquitination system of at least $10^2$ $M^{-1}$ and a target protein binding peptide element that is able to bind specifically to a target protein wherein the target protein binding peptide element has a molecular weight of less than 30,000 and has a binding affinity for the target protein greater than $10^2$ $M^{-1}$ where the ubiquitination recognition peptide element is covalently linked to the target protein binding peptide element.

The invention also provides a method of modulating the level and/or activity of at least one target protein in an eukaryotic cell via the modulation of ubiquitination of the at least one target protein comprising contacting the cell with a compound comprising; a ubiquitination recognition element which is able to bind to either the E3 or E2 elements of the ubiquitination system, wherein the ubiquitination recognition element has a molecular weight less than 30,000 and has a binding affinity for the E3 and/or E2 elements of the ubiquitination system of at least $10^2$ $M^{-1}$ and; a target protein binding element that is able to bind specifically to a target protein wherein the target protein binding element has a molecular weight of less than 30,000 and has a binding affinity for the target protein greater than $10^2$ $M^{-1}$, the ubiquitination recognition element is covalently linked to the target protein binding element.

The invention also provides a method of treating an infection in a mammal comprising administering to the mammal an amount of a compound sufficient to eliminate and/or reduce the infection comprising contacting the mammal with a compound comprising; a ubiquitination recognition element which is able to bind to either the E3 or E2 elements of the ubiquitination system, wherein the ubiquitination recognition element has a molecular weight less than 30,000 and has a binding affinity for the E3 and/or E2 elements of the ubiquitination system of at least $10^2$ $M^{-1}$ and; a target protein binding element that is able to bind specifically to a target protein wherein the target protein binding element has a molecular weight of less than 30,000 and has a binding affinity for the target protein greater than $10^5$ $M^{-1}$, wherein the ubiquitination recognition element is covalently linked to the target protein binding element.

The invention is also a method of treating cancer or tumor in a mammal comprising administering to the mammal an amount of a compound sufficient to reduce the size of the tumor comprising contacting the mammal with a compound comprising; a ubiquitination recognition element which is able to bind to either the E3 or E2 elements of the ubiquitination system, wherein the ubiquitination recognition element has a molecular weight less than 30,000 and has a binding affinity for the E3 and/or E2 elements of the ubiquitination system of at least $10^2$ $M^{-1}$ and; a target protein binding element that is able to bind specifically to a target protein wherein the target protein binding element has a molecular weight of less than 30,000 and has a binding affinity for the target protein greater than $10^5$ $M^{-1}$, wherein the ubiquitination recognition element is covalently linked to the target protein binding element.

The invention also provides a method of generating a compound which comprises covalently linking a target protein binding element to a ubiquitination recognition element.

DETAILED DESCRIPTION OF THE INVENTION

The present invention relates to a method of development of compounds which are active via a new mechanism of action. The invention is to a new class of molecules that make use of the targeted modification and/or degradation of proteins to modulate a selected target protein's concentration and/or activity. This is achieved through the construction of a bi-functional molecule. This control of protein levels is achieved using an exogenous molecule able to affect ubiquitination of a given protein. The ubiquitinated protein is targeted for intracellular degradation via normal cellular pathways.

Figure 1:
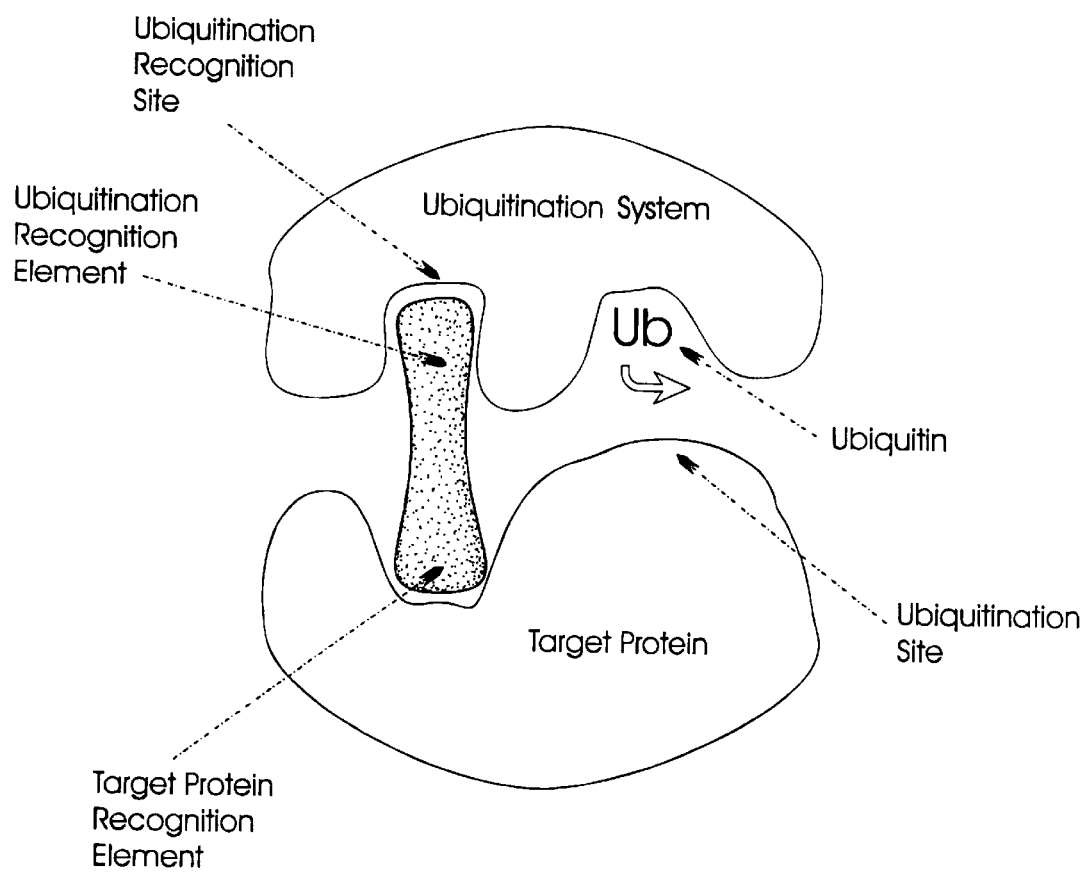
FIG. 1 shows the basic elements of the invention, where a molecule containing a ubiquitination recognition element and a target protein recognition element brings together the target protein and a ubiquitination system to stimulate the ubiquitination of the target protein by the ubiquitination system.

The exogenous molecules able to selectively target ubiquitination of a pre-selected protein comprise; a ubiquitination recognition element and target protein binding element for a pre-selected protein covalently linked to form the compositions of the invention (FIG. 1).

The ubiquitination recognition element is designed to interact with the ubiquitination mechanisms of the cell allowing their recruitment. The target protein binding element binds to a pre-selected protein in order to effectively present the ubiquitin recognition element.

DEFINITIONS

Ubiquitin, as used herein is a protein which is functionally and structurally related to cellular ubiquitin. The functionally activity is defined via its conjugation to other proteins forming covalent protein conjugates through the action of an ATP dependent cellular pathway and its protein sequence. The structural relation is defined either by sequence homology and/or structure homology. Sequence homology is defined by a BLAST sequence homology analysis (Altschul S F et al., J Mol Biol 1990, 215, 403–410) where the E value is less than 0.063, representing a significant homology. Structural homology is defined by a VAST homology analysis where the p-value is less than 0.0001, representing a significant homology.

Ubiquitination, as used herein is the formation of a covalent bond between a cellular protein and a ubiquitin protein (as defined above) through the action of an ATP dependent cellular pathway.

Ubiquitination system, as used herein is a cellular system able to direct the formation of covalent protein conjugates between ubiquitin and other proteins. Ubiquitination systems consist of one or a number of proteins involved in the activation of ubiquitin, recognition of a protein for ubiquitination and formation of ubiquitin:protein conjugates.

Ubiquitination recognition element, as used herein is a chemical moiety which is able to bind with a ubiquitination systems proteins or its component proteins. This binding is further defined by the ability of the chemical moiety to promote the ubiquitination of a protein attached directly or indirectly to the moiety.

Ubiquitination recognition peptide element, as used herein is a peptide moiety which is able to bind with a ubiquitination systems proteins (other than those of the N-end rule) or its component proteins. This binding is further defined by the ability of the peptide moiety to promote the ubiquitination of a protein attached directly or indirectly to the moiety.

Ubiquitination recognition site, as used herein is a sequence of a protein which is known to act as the recognition site for ubiquitination systems. This ubiquitination recognition site is further defined by the ability of the site to promote the ubiquitination of a protein attached directly or indirectly to the site.

Target protein, as used herein is a protein selected for ubiquitination using a compound of the subject invention.

Target protein binding element, as used herein is a chemical moiety which is able to bind to a target protein. Examples of these binding elements include drugs and toxin molecules.

Target protein binding peptide element, as used herein is a peptide structure which is selected to bind to a target protein.

The means by which the compositions of the invention are identified and synthesized is described below.

The invention solves problems of library construction and screening by making use of the binding activity of a small molecule to develop biologically active and valuable molecules. This removes the problems associated with the synthesis of chemical libraries in that a) the compounds can be screened bound to solid phase (in fact an advantage of the subject invention) and b) the presence of a linker element is a utility of the subject invention which is commonly a problem in solid phase chemistries. These specific advantages in combination allow for an optimal route to the generation of chemical libraries and their screening. These two elements combine synergistically resulting in rapid drug development. In addition to these advantages, the hit rates for active compounds is increased as generalized binding is optimal, not just binding to the active site which limits the potential drug compounds which may be found following conventional drug screening approaches. The invention also allows for the development of small molecule drugs whose development is problematic using traditional methods, for example finding a small molecule which can block the interaction of two large proteins such as is seen with cell cell interactions, some receptor ligand interactions, and intra cellular signaling pathways.

Since the method of the subject invention does not make use of the 'active' site of a given target protein, it is able to achieve a level of specificity for a drug molecule previously considered extremely difficult and uncertain using conventional drug discovery efforts. This advantage stems from the constraints placed on existing drug discovery efforts that are based on the need to inhibit an enzyme or receptor binding site that is common to a series of different proteins in different tissues and with very different roles in the physiology of the organism. These constraints are based on the common structural elements in the binding or catalytic sites of these related proteins which form the site for conventional drug discovery. The common structural elements typically result in the selection of drugs that will inhibit the whole series of different proteins as these structural elements form the basis for the binding of the drug molecules selected from the screen. Thus conventional drug screening approaches result in the selection of drug hits which do not provide the degree of selectivity desired to bring about a desired therapeutic affect. In the subject invention, since the active site does not need to be the target for the selection of molecules that form the basis of the drug molecule, a significant improvement in the discovery of highly selective drugs is achieved. The consequence is the development of drugs with an enhanced therapeutic value. This advantage is further enhanced by the ability of this drug discovery approach to make use of the whole surface of the given protein target to find molecules with the desired binding specificity. This advantage is then combined with the ability to make use of a rapid screen that is wholly based on the use of binding and thus achieves a level of speed and through put not possible with other methods. This advantage is of great value when the desire is to find a very specific inhibitor of a given member of a protein family that is highly homologous and thus extremely difficult or impossible for drug discovery based on the effector, receptor or catalytic site of the given protein. This invention thus provides a means for the development of compounds of the invention which are variously; therapeutics, have various pharmacological activities, herbicides, pesticides, insecticides, antivirals, antifungals, anti-parasitics and are able to selectively modify the performance of an organism.

The subject invention also includes a method to enhance the immunogenicity of a given protein. This is achieved by enhancing the degradation of a given protein via the 26S proteasome by selective ubiquitination resulting in increased presentation of the antigen as peptides in the context of MHC I. The ability to enhance the immunogenicity of a given protein has great value in the treatment of infectious diseases (HIV, HBV, HCV, Herpes, etc) and also in the treatment of cancer where the cancer antigen is not very immunogenic. The use of this approach for cancer treatment in combination with cancer vaccine approaches and/or use of cytokines such as gamma interferon, is also contemplated.

The subject invention also provides a method whereby a small molecule is used to regulate the levels of a protein genetically engineered into a cell line or organism. This is achieved via the modification of a gene encoding the protein of interest to contain, in addition to the desired activity of the protein, a binding site for a small molecule able to activate targeted covalent modification. This modified nucleic acid encoding an protein is then used to generate a genetically engineered cell or organism. This approach allows for the specific modulation of a given proteins action after the production of a genetically modified cell or organism on addition of compounds of the invention able to activate targeted covalent modification.

The subject invention also permits the development of specific compounds of the invention which can be used to target specific proteins for degradation to allow the determination of a given proteins role within the cell or organism. This approach is useful in target validation for the development of pharmaceuticals, for conducting basic research and for target validation for may other discovery efforts directed to the discovery of molecules able to bring about modulation of an amino acids levels and/or function.

TARGET PROTEIN BINDING ELEMENTS

The target protein binding elements of the invention are molecular structures which bind target proteins, and are used in the compounds of the invention to target the ubiquitination recognition elements to the target protein. These target protein binding elements are covalently linked to the ubiquitination recognition elements to form the compounds of the invention and provide the linkage between these two elements of the compounds of the invention. When the target protein binding element of a compound of the invention binds to a given target protein it presents the ubiquitination recognition element to allow the activation of the ubiquitination pathway and subsequent ubiquitination of the target protein bound by the target protein binding element.

Target protein binding elements are small organic molecules defined by binding to a predetermined target molecule, having a molecular weight from 50 to 30,000 and with a binding affinity of greater than $10^5$ $M^{-1}$ for the target protein of interest. The binding affinity in an advantageous embodiment is greater than $10^6$ $M^{-1}$. The molecular weight in an advantageous embodiment is between 50 and 3,000. The binding affinity in a more advantageous embodiment is greater than $10^8$ $M^{-1}$. The molecular weight in a more advantageous embodiment is between 100 and 2,000. Most drugs are typically either neutral, weak acids or bases. Examples of known specific drugs are phenytoin (pKa of 8.3) and aspirin (pKa of 3.0).

Also target protein binding elements can be selected based on having at least one the following characteristics;

less than 50 H-bond donors, MW less than 5,000, ClogP or MLogP (calculated log P, based on the Pomona College Medicinal Chemistry program ClogP or using Molecular Design Limited MACCS and ISIS based programs MlogP, logP (the logarithm of the octanol/water partition coefficient) less than 6, sum of N's and O's (a rough measure of H-bond acceptors) less 100.

Also target protein binding elements can be selected based having on at least one the following characteristics; less than 5 H-bond donors, MW less than 500, ClogP or MLogP less than 5, sum of N's and O's (a rough measure of H-bond acceptors) less 10.

Also target protein binding elements can be selected based on having two or more combinations of the following characteristics; less than 5 H-bond donors, MW less than 500, ClogP or MLogP less than 5, sum of N's and O's (a rough measure of H-bond acceptors) less 10 (Lipinski C A, 1997, Adv. Drug Delivery Rev. 23, 3–25).

These target protein binding elements are different from peptides, proteins and DNA and RNA in that they are not highly charged or polar, are readily absorbed into the body due to the size and hydrophobicity. Also one of the other key properties of target protein binding elements is the stability relative to proteins which are stable within narrow ranges of temperature, pH and ionic strength due to the need to maintain a give structural conformation of the folded polypeptide chain. Peptides although not as sensitive to the physical properties of an environment are relatively unsuitable as drugs due to the poor biological stability, short half-life and poor bioavailability within cells and are not considered compounds of the invention.

Some examples of molecules which have moieties desired in a target protein binding element include drug molecules and molecules selected for binding and/or inhibition of various proteins functions, for example; fluorescein, biotin, antigens, L-deprenyl, Omeprazole, Clavulanate, organoarsenical compounds such as 4',5'-bis(1,3,2-dithioarsolan-2-yl)fluorescein, p-aminophenylarsine oxide, p-aminophenylarsine oxide, chicoric acid, captopril, enalapril, lovastatin, proscar, indinivar, zileuton, L-372,460 (J. Med Chem 41, 401, 1998), apomorphine, N-n-propylnorapomorphine, dihydrexidine, quinpirole, clozapine, haloperidol, nitrocaramiphen, and iodocaramiphen.

It is evident from the small sample above that numerous examples exists of chemistries which could form the basis of chemistries for target protein binding element. Also the numerous nature of these potential target protein binding elements is illustrative of the potential ease with which such moieties can be discovered using routine experimentation.

Compounds of the invention include small molecules used in veterinary, agricultural, food and environmental applications where a biological effect is generated. Examples of compounds of the invention are fungicides, herbicides, pesticides, algaecides, insecticides, anti-virals, anti-parasitics etc. In addition compounds of the invention are also molecules able to form covalent bonds with the target proteins of interest, such as suicide inhibitors. Examples of well know drugs able to from covalent bonds, are as follows; L-deprenyl (Gerlach, M et al 1992, Eur. J. Pharmacol. 226, 97–108), Omeprazole (Howden, C W. 1991, Clin. Pharmacokinet, 20, 38–49) and Clavulanate (Neu, H C. 1990, J. Am. Acad. Dermatol, 22, 896–904). In addition to these well known molecules are a considerable number of other small molecules known to form covalent bonds specifically with various proteins. Also considered compounds of the invention are enzyme substrates that are used to covalently modify proteins (such as farnesylation, phosphorylation, glycosylation, and gerenylation), where the natural enzyme substrate is modified in such a way that it contains a ubiquitination recognition element.

TARGET PROTEIN BINDING PEPTIDE ELEMENTS

The target protein binding peptide elements of the invention are peptide structures which are selected to bind to target proteins and are used in the compounds of the invention to target the ubiquitination recognition elements, excluding those based on the N-end rule, to the target protein. These target protein binding peptide elements are covalently linked to the ubiquitination recognition elements, excluding those based on the N-end rule to form the compounds of the invention and provide the linkage between these two elements of the compounds of the invention. When the target protein binding peptide element of a compound of the invention binds to a given target protein it presents the ubiquitination recognition element to allow the activation of a ubiquitination pathway (not based on the N-end rule) and subsequent ubiquitination of the target protein bound by the target protein binding peptide element. Examples of these are peptide selected from combinatorial libraries such as those expressed on the surface of phage (Yanofsky S D et al., Proc. Natl. Acad. Sci USA 1996, 93, 7381).

Examples of target protein binding peptide elements include;

epsilon-aminocaproic acid-phospho-Y-E-E-I (SEQ ID #56) binding to src SH2 domain;

DREGCRRGWVGQCKAWFN (SEQ ID #57) binding to erythropoietin;

ETPTFTWEESNAYYWQPYALPL (SEQ ID #58) binding to IL-1alpha;

TFVYWQPYALPL (SEQ ID #59) binding to IL-1alpha;

VSLARRPLPPLPGGK (SEQ ID #60) binding to the SH3 domains of Src, Fyn, Lyn, Yes, P13K;

KGGGAAPPLPPRNRPRL (SEQ ID #61) binding to the SH3 domains of Src, Fyn, Lyn, Yes;

AECHPQGPPCIEGRK (SEQ ID #62) binding to streptavidin;

GACRRETAWACGA (SEQ ID #63) binding to alpha5betal integrin;

DITWDQLWDLMK (SEQ ID #64) binding to E-selectin;

RNMSWLELWEHMK (SEQ ID #65) binding to E-selectin;

TARGETS OF THE TARGET PROTEIN BINDING ELEMENT

Targets of the target protein-binding element are numerous and are selected from proteins and proteins that are expressed in a cell such that at least a portion of the sequences is available within the cell. The term protein includes all sequences of amino acids greater than two and includes peptides. Below is a partial list of target proteins. Any protein in eukaryotic cells are targets for ubiquitination mediated by the compounds of the invention. Those of special interest are those which are involved in diseases or disease processes included; are infectious diseases of viral, microbial, and parasitic nature, metabolic diseases, aging, environmental diseases, genetic diseases, life style diseases. Also protein targets which are involved in performance enhancement are also targets, such as those involved in growth and development, memory, and sensory perception.

Examples of viruses contemplated as targets of the subject invention are HIV1, HIV2, HLTV, CMV, HPV, HSV, hepatitis, HBV, HCV, HAV, HDV, HGV, influenza A, influenza B, influenza C, rhinoviruses, rotaviruses, entroviruses, Ebola, polio, chicken pox, RSV, coronavirus, adenoviruses, parainfluenza 3, coxsackie A, and epstein-barr virus.

The following are example of targets of the target protein binding elements of the subject invention, which include:

Receptors

CD124, B7.1 and B7, TNFR1m(p55), TNFR2 (p75), Bcl/Bax and other partners in the apotosis pathway, C5a receptor, CXCR1, CXCR2, 5HT receptors, dopamine receptors, G proteins, ie Gq, histamine receptors, chemokine receptors, JAK/STAT cf ligand, RXR and similar, CD4, CD5, IL-2 receptor, IL-1 receptor, TNF-alphaR, ICAM1, VCAM, VLA-4 integrin, selectins, CD40/CD40L, neurokinins and receptors, Ras/Raf/MEK/ERK pathway, vascular endothelial growth factor, oxytocin receptor, microsomal transfer protein inhibitor, angiotensin II, glycine receptor, noradrenaline reuptake receptor, endothelin receptors, neuropeptide Y and receptor, adenosine receptors, purinergic receptors (P2Y1, P2Y2, P2Y4, P2Y6, P2X1-7), TrkA a receptor for NGF, beta-amyloid, tyrosine kinase Flk-1/KDR, vitronectin receptor, integrin receptor, Her-2/neu, MCH receptor, IL-4 receptor alpha chain and the Toll-like receptors and human homologue, FKHR and AFX or the human homologues of daf2, daf 16 and age 1.

Enzymes

NADPH oxidase, HMG-CoA reductase, PDE V phosphodiesterase type, PDE IV phosphodiesterase type 4, PDEI, PDEII, PDEIII, squalene cyclase inhibitor, nitric oxide (NO) synthase, cyclo-oxygenase 1, cyclo-oxygenase 2,5-lipoxygenase, tryptase serine protease, thymidylate synthase, purine nucleoside phosphorylase, GAPDH trypanosomal, glycogen phosphorylase, Carbonic anhydrase, HIV 1 protease, HIV 1 integrase, influenza, neuraminidase, hepatitis B reverse transcriptase, tyrosine kinases, CD23, tyrosine kinase p56 lck, inosine monophosphate dehydrogenase, p38 MAP Kinase, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-1) protease, cytomegalovirus (CMV) protease, poly (ADP-ribose) polymerase, cyclin dependent kinases, 5 alpha reductase inhibitors, adenosine kinase and AMP deaminase, farnesyltransferases, geranylgeranyl transferase, telomerase, cytosolic phospholipase A2, EGF receptor tyrosine kinase.

Membrane Transporters

Sodium channel, $Ca^{++}$ channels, multi drug resistance (MDR), protein P-glycoprotein (and MRP), bile acid transporter.

Insecticide target examples include, ecdysone 20-monooxygenase, ion channel of the GABA gated chloride channel, acetylcholinesterase, voltage-sensitive sodium channel protein, calcium release channel, and chloride channels.

Herbicide target examples include Acetyl-CoA carboxylase, adenylosuccinate synthetase, protoporphyrinogen oxidase, and enolpyruvylshikimate-phosphate synthase.

Targets for anti-parasitic drug development include: Leishmania, proteins of the sterol synthesis pathway: Plasmodium, dihydrofolate reductase; dihydrofolate reductase-thymidylate synthase (bifunctional) resistance known due to mutations in the gene for this enzyme, heme polymerase: Trypanosoma, ornithine decarboxylase, trypanothione reductase, Ornithine decarboxylase of the trypanosoma represents an ideal candidate for destruction due to its long half-life and low turn over in trypanosoma. It has also been suggested that the shikimate pathway, which is a target for herbicide development, would also be of value in the development of anti-parasitics for parasites of the phylum Apicomlexa (ie. Plasmodium falciparum, Cryptosporidium parvum and Toxoplasma gondii) as it absent from mammals.

Also considered targets of the subject invention are proteins that are involved in the performance of a cell and/or organism. Performance characters of a cell and/or organism are those characters which are considered desirable traits which a cell and/or organism has in some part. These performance characters may be present in other cells or organisms and be desired in cells and/or organisms which do not posses them. Examples of what are considered performance characters are, flower color, fragrances, specific shapes and colors in organisms such a cats and dogs, disease resistance, growth rates, size, taste, alcohol yield from yeast. Thus performance characters are generally things that are desired in cells and organisms used either in the production of desired products or in the production of esthetical value (look, taste, feel, smell and sound).

In the case of flower color (considered an esthetical value), the proteins involved in the biosynthesis of flavonoids, carotenoids and anthocyanins; including flavanone 3-hydroxylase, anthocyanin synthase, dihydroflavonol 4-reductase, flavonoid 3',5'-hydroxylase, anthocyanin 5-aromatic acyltransferase, UDP-glucose: flavonoid 3-O-glucosyltransferase, anthocyanin rhamnosyltransferase, anthocyanin 3'-methyltransferase, anthocyanin 3'5'-methyltransferase, leucoanthocyanidin dioxygenase, anthocyanidin synthase, anthocyanin acyltransferase, chalcone synthase, chalcone flavanone isomerase, glutathione S-transferase, one considered as targets of the subject invention involved in performance characteristics. In addition to the proteins involved in the synthesis of flower color, the proteins involved in the regulation of the expression of the synthases and other proteins involved in the production of flower color are also considered targets of the subject invention. Examples of the regulatory genes include the R and C1 gene families, an2 and jaf13, the delila gene. Quattrocchio F. 1998, Plant J. 13(4), 475–488.

Other potential target molecules of the subject invention include targets as described above but also targets in all eukaryotic organisms. Potential targets exist in agriculture, veterinary and environmental fields. For example in the agricultural field, molecules which are selective in action and non-toxic are highly desirable for use as herbicides, anti-virals, anti-parasitics, growth modulators and drugs; thus target molecules can be selected from certain animals, plants, viruses and parasites of interest to agriculture. In the veterinary field anti-virals, anti-parasitics, antibiotics, growth modulators, anti-inflammatory and drugs are of interest and target molecules can be selected from certain animals, viruses and parasites of interest in veterinary science. In the environmental field the potential targets are the same as for agricultural but the aims are to control selectively certain populations either positively as in the case of an endangered species but also negatively where a population has expanded its environment or where a foreign organism is undesirable to a given ecosystem. Thus it is understood by those skilled in the art that the ability to modulate the level of a selected target molecule could have wide ranging effects in very diverse areas of science, technology and human endeavors.

UBIQUITIN

In this invention ubiquitin includes ubiquitin and ubiquitin like sequences related either by sequence homology, by structural homology or functional homology or having been described as related to ubiquitin in the scientific literature. Functional homology to ubiquitin is defined based on a proteins ability to be attached covalently to other proteins via an ATP dependent enzyme system, proteins transferred in this way are considered to be ubiquitin in this invention and the protein coupling step is considered to be ubiquitination. In the case of sequence homology protein sequences with a BLAST (Altschul S F et al., J Mol Biol 1990, 215, 403–410) E (Expected) value of 0.063 or less are considered in this invention to be ubiquitin. The BLAST search being run the NIH web server (NIH, http://www.ncbi.nlm.gov). The E value is a parameter that describes the chances of finding a sequence match based on chance. Thus the smaller the value the smaller the chance that the match occurred by chance. In the case of structural homology these are determined based on the VAST (NIH, http://www.ncbi.nlm.gov) analysis to yield p-value of less than 0.0001 are considered to be ubiquitin in this invention. The VAST (NIH, http.//www.ncbi.nlm.gov) p-value is a measure of the significance of a comparison, expressed as a probability. For example if the p-value is 0.0001 then the odds are 10,000 to 1 against seeing a match by chance.

A number of systems are also considered to be ubiquitination pathways in this invention as these protein modification pathways, involved in the attachment of Apg12, Rub1/Nedd8 and Smt3/SUMO-1 are generally considered as being equivalent to the ubiquitin pathway due to their functional homology to the ubiquitination pathway.

In these systems homology at the level of sequence is seen but also clear parallels can be drawn based on the functional elements involved in the various systems (S Jentsch and H. D. Ulrich, Nature (1998) 395, 321–322).

In the case of the Apg12 system this protein is involved in the autophagy of various cellular components. Apg12 appears to be the functional homologue of ubiquitin and is transferred via Apg7 and Apg10 the functional homologue of the E1 and E2 conjugating enzymes of the ubiquitin and final is used to modify Apg5 to activate autophagy possible via a targeting mechanism. The analysis of the sequence of Apg7 shows a considerable homology to the E1 enzymes of the ubiquitin pathway.

In the case of Rub1/Nedd8 system these proteins are involved in a regulatory role. The Smt3/SUMO-1 system is also involved in the targeting of proteins.

ANTIGENS

Antigens of this invention are considered to be target proteins of the subject invention. Antigens of the invention are proteins that are derived from numerous sources, examples of which are intracellular proteins of the host, or other target organisms. The antigens can also be derived from other organisms and are presented intracellularly within the organism of interest. Typically these antigens are derived from an infectious organism such as a virus, bacteria or fungi or derived from a normal protein or one mutated in a given disease tissue. In one embodiment of the invention antigens present in cancer cells are utilized. Example of cancer antigens include MAGE 1, MAGE 2, MAGE 3, tyrosinase, tyrosinase related protein 1 and 2, Pmel H. In the case of viruses examples of antigens are proteins for example from HCV, HIV, HPV, HBV, influenza, rhinoviruses.

UBIQUITINATION RECOGNITION ELEMENTS

In order to develop the compounds of the invention for targeted ubiquitination, identification of a chemical element able to replace the targeting and/or signaling activity of the N-terminal amino acid of a protein or a sequence element of a protein, which result in the ubiquitination of the protein, is required. A number of chemical entities 'ubiquitination recognition elements' have already been described which interact with the ubiquitination system of the cell; a number of di-peptides, and some modified amino acids. These compounds have been described based on the ability to inhibit the activity of the ubiquitination pathway based on the known activating amino acids from the N-end rule. These include dipeptides, amino acid hydroxamates, and amino acid methyl esters with small uncharged, basic or bulky hydrophobic N-terminal residues (Gonda et al 1989, J Biol. Chem. 264: 16700). In addition sequence elements have been defined which include, 'destruction box' or D box, PEST motifs, Deg1, Deg2, delta ($\delta$) domains, and phosphorylated sequences which also target ubiquitination. Also considered as ubiquitination recognition elements are oxidized derivatives of peptides. These compounds are useful in the present invention. Examples of oxidized amino acid are oxidized methionine to form methionine sulfoxide, oxidized leucine to form hydroxyleucine, oxidized tryptophan to form N-formyl-kynurenine, and oxidized tyrosine to form 3,4-dihydroxyphenylalanine.

It is also understood that identification of new ubiquitination recognition elements is possible using standard methods for drug discovery (as outlined below) based on modulation of the ubiquitination pathways. Methods of screening compounds which can be used as ubiquitination recognition elements has been demonstrated for dipeptides, amino acid hydroxamates, and amino acid methyl esters with small uncharged, basic or bulky hydrophobic N-terminal residues and also large chemical libraries (U.S. Pat. No. 5,766,927; WO 98/23283; GB 2,320,570 Gonda et al 1989, J Biol. Chem. 264: 16700). In one specific example a compound was identified 'compound of example 2' (1-chloro-2,4-bis{4-[2-chloro-6-(5-(2,7-disulfo-4-hydroxy-3-(2-(1-sulfonaphthyl)azo)naphthyl)amino)-1,3,5-triazinyl]amino}benzene), of patent application GB 2,320,570 (which is hereby incorporated by reference in its entirety), which inhibited an E2 ubiquitination reaction indicating its utility as a ubiquitination recognition element of the subject invention; here in called compound Z. Other equivalent methods for identification of chemical elements equivalent to the PEST, Deg and other sequence elements based on the assays for ubiquitination systems (Hochstrasser M and Varshavsky A 1990, Cell 61; 697–708) can be used. In the case of the PEST sequence from ornithine decarboxylase (amino acids 422–462), this sequence has been fused to a green fluorescent protein sequence to generate a fluorescent protein which has a half life of only 2 hours from its original >24 hours making this an ideal system in which to detect molecular equivalent of the PEST sequence. In addition to specific molecular species which interact with the E3 elements of the ubiquitination pathway, it is also contemplated that specific molecular species that interact with the E2 elements of the ubiquitination pathway can be used in an equivalent way to target selective ubiquitination. A specific example of an E2 domain that is involved in targeting specific ubiquitination is the C-terminal domains of E2. Thus chemical elements able to bind to the E2's and especially the C-terminal domains of E2 are considered ubiquitination recognition elements of the subject invention. The elements that interact with the E2 elements have been defined as various sequence elements (parts) of proteins that control their ubiquitination.

Analysis of the E3s has determined common themes in structure and function. The basic function for E3s is the recognition of a protein substrate for ubiquitination. This is achieved either as a single protein or as a multi-protein complex. In some cases the E3s are single proteins which typically depend on E2 to mediate the ubiquitination. In the case of one class of E3s known as SCF complexes (containing Skp1p, Cdc53p and F-box proteins in a complex) it is known that the F-box proteins act as the substrate specific adapters to recruit various substrates to the complex for ubiquitination. Thus in these E3s it is the interaction of the F-box proteins with the proteins targeted for ubiquitination, the ubiquitination is achieved through Cdc-34p (E2). The above description of the ubiquitination elements has drawn on general names for the elements such as E1, E2 and E3 but also some specific names of the proteins in a given system. It will be understood by those skilled in the art that equivalent proteins, as determined by function and sequence homology exist and can be considered to be equivalent (Patton E E, et, al. Trends Genet, 1998 14, 236–243).

Thus it is clear to those skilled in the art that binding molecules which bind to the ubiquitination recognition site (FIG. 1) of the ubiquitination system can be selected and identified using art known methods and available chemical libraries. In the absence of available chemical libraries, synthesis of equivalent chemical libraries can be done following art known methods, as described below for the discovery of ubiquitination recognition elements of the subject invention.

Examples of PEST sequences include,

MEFMHISPPEPESEEEEEHS (SEQ ID NO 1),

MEFMHESHSS (SEQ ID NO 2),

MEFMHISPPEPESHSS (SEQ ID NO 3),

MEFMHESEEEEEHSS(SEQ ID NO 4),

MEASEEEEEF (SEQ ID NO 5),

HGFPPEVEEQDDGTLPMSCAQESGMDRH (SEQ ID NO 6),

HGFPPAVAAQDDGTLPMSCAQESGMDRH (SEQ ID NO 7),

HGFPPEVEEQDDGALPMSCAQESGMDRH (SEQ ID NO 8),

HGFPPEVEEQDDGTLPMSCAQESGMDHH (SEQ ID NO 9),

HGFPPEVEEQDVGTLPMSCAQESGMDRH (SEQ ID NO 10),

HGFPPEVEEQDVGTLPISCAQESGMDRH (SEQ ID NO 11),

HGFPPEVEEQDASTLPVSCAWESGMKRH (SEQ ID NO 12),

FPPGVEEPDVGPLPVSCAWESGMKRH (SEQ ID NO 13),

FLAEVEEQDVASLPLSCACESGIEYPA (SEQ ID NO 14), expressed as a following consensus

FXXEVEEQDXXXLPXSCAXESGXX(X) (SEQ ID NO 15),

FXXAVAAQDXXXLPXSCAXESGXX(X)X (SEQ ID NO 16), or

HGXXPEVX(XX)DXXXLXXSCAQESGMXXX (SEQ ID NO 17), where X is any amino acid and (X) is an optional amino acid.

Examples of D boxes include,

RHALDDVSN (SEQ ID NO 18),

RLALNNVTN (SEQ ID NO 19),

RAALGDVSN (SEQ ID NO 20),

RQVLGDIGN (SEQ ID NO 21),

RAALGDLQN (SEQ ID NO 22),

RAALGNISN (SEQ ID NO 23),

RNTLGDIGN (SEQ ID NO 24),

RTALGDIGN (SEQ ID NO 25),

RAALGEIGN (SEQ ID NO 26),

RAVLEEIGN (SEQ ID NO 27),

RSAFGDITN (SEQ ID NO 28),

RSILGVIQS (SEQ ID NO 29),

RAALGVITN (SEQ ID NO 30),

RTVLGVIGDN (SEQ ID NO 31),

RTVGVLQEN (SEQ ID NO 32),

RAALGTVGE (SEQ ID NO 33),

RTVLGVLTEN (SEQ ID NO 34),

RAALAVLKSGN (SEQ ID NO 35),

RLPLAAKDN (SEQ ID NO 36),

RQLFPIPLN (SEQ ID NO 37),

RRTLKVIQP (SEQ ID NO 38), expressed as a general structure R(A/T)(A)LGX(I/V)(G/T)(N) (SEQ ID NO 39), or expressed as a consensus RXXLGXIXN (SEQ ID NO 53), where X is any amino acid and amino acids in parentheses occur in more than 50% of known destruction sequences.

Examples of other ubiquitination recognition elements are;

KEFAVPNETSDSGFISGPQSS (cactus) (SEQ ID NO 40),

KGPDEAEESQYDSGLESLRSLR (IkBepsilon) (SEQ ID NO 41),

KAADADEWCDSGLGSLGPDA (IkBbeta), (SEQ ID NO 42), KKERLLDDRHDSGLDSMKDEE (IkBalpha), (SEQ ID NO 43), with a consensus of KX(8–10)DSG(hydrophobic amino acid)XS (SEQ ID NO 44), where the S in bold are phosphorylated. In addition to the signals associated with NF kB activation are the related ubiquitination recognition elements SYLDSGIHSGAT (SEQ ID NO 45), (human beta-catenin) and RAEDSGNESEGE (SEQ ID NO 46), (HIV-1 Vpu) where the S in bold are phosphorylated.

The identified and/or discovered chemical entities which bind to the sites on the E3 and/or E2 elements involved in recognition prior to ubiquitination are the ubiquitination recognition elements of the subject invention. The ubiquitination recognition elements are thus functionally defined by their ability to compete for binding of the natural recognition signals for ubiquitination with their ubiquitination partners, have a molecular weight less than 30,000; 50 to 10,000; 50 and 3,000; 100 and 3,000; 200 and 3,000, are capable of being linked to other molecular species and retain their ability to compete for binding of the natural recognition signals for ubiquitination with their ubiquitination partners. In addition the binding affinity of these ubiquitination recognition elements is typically greater than $10^2$ $M^{-1}$. The binding affinity in a advantageous embodiment is greater than $10^3$ $M^{-1}$. The binding affinity the most advantageous embodiment is greater than $10^4$ $M^{-1}$.

Some examples of ubiquitination recognition elements based on the N-recognin include;

Arg-εAhx-Cys

Arg-β-Ala-εAhx-Cys

Arg-βAhx-εAhx-Cys

Phe-εAhx-Cys

Phe-β-Ala-εAhx-Cys
Phe-βAhx-εAhx-Cys
Arg-Ala-εAhx-Cys
Arg-Ala-β-Ala-εAhx-Cys (SEQ ID No:66)
Arg-Ala-εAhx-εAhx-Cys
Phe-Ala-εAhx-Cys
Phe-Ala-β-Ala-εAhx-Cys (SEQ ID NO:67)
Phe-Ala-εAhx-εAhx-Cys

UBIQUITINATION RECOGNITION PEPTIDE ELEMENT

Ubiquitination recognition peptide element, is defined as a peptide based moiety which is able to bind with a ubiquitination systems proteins (other than those of the N-end rule) or its component proteins. This binding is further defined by the ability of the peptide moiety to promote the ubiquitination of a protein attached directly or indirectly to the moiety.

Examples of such ubiquitination recognition peptide elements are;

MEFMHISPPEPESEEEEEHS (SEQ ID NO 1),
MEFMHESHSS (SEQ ID NO 2),
MEFMHISPPEPESHSS (SEQ ID NO 3),
MEFMHESEEEEEHSS(SEQ ID NO 4),
MEASEEEEEF (SEQ ID NO 5),
HGFPPEVEEQDDGTLPMSCAQESGMDRH (SEQ ID NO 6),
HGFPPAVAAQDDGTLPMSCAQESGMDRH (SEQ ID NO 7),
HGFPPEVEEQDDGALPMSCAQESGMDRH (SEQ ID NO 8),
HGFPPEVEEQDDGTLPMSCAQESGMDHH (SEQ ID NO 9),
HGFPPEVEEQDVGTLPMSCAQESGMDRH (SEQ ID NO 10),
HGFPPEVEEQDVGTLPISCAQESGMDRH (SEQ ID NO 11),
HGFPPEVEEQDASTLPVSCAWESGMKRH (SEQ ID NO 12),
FPPGVEEPDVGPLPVSCAWESGMKRH (SEQ ID NO 13),
FLAEVEEQDVASLPLSCACESGIEYPA (SEQ ID NO 14), expressed as a following consensus
FXXEVEEQDXXXLPXSCAXESGXX(X) (SEQ ID NO 15),
FXXAVAAQDXXXLPXSCAXESGXX(X)X (SEQ ID NO 16), or
HGXXPEVX(XX)DXXXLXXSCAQESGMXXX (SEQ ID NO 17), where X is any amino acid and (X) is an optional amino acid.

Examples of D boxes include,
RHALDDVSN (SEQ ID NO 18),
RLALNNVTN (SEQ ID NO 19),
RAALGDVSN (SEQ ID NO 20),
RQVLGDIGN (SEQ ID NO 21),
RAALGDLQN (SEQ ID NO 22),
RAALGNISN (SEQ ID NO 23),
RNTLGDIGN (SEQ ID NO 24),
RTALGDIGN (SEQ ID NO 25),
RAALGEIGN (SEQ ID NO 26),
RAVLEEIGN (SEQ ID NO 27),
RSAFGDITN (SEQ ID NO 28),
RSILGVIQS (SEQ ID NO 29),
RAALGVITN (SEQ ID NO 30),
RTVLGVIGDN (SEQ ID NO 31),
RTVGVLQEN (SEQ ID NO 32),
RAALGTVGE (SEQ ID NO 33),
RTVLGVLTEN (SEQ ID NO 34),
RAALAVLKSGN (SEQ ID NO 35),
RLPLAAKDN (SEQ ID NO 36),
RQLFPIPLN (SEQ ID NO 37),
RRTLKVIQP (SEQ ID NO 38), expressed as a general structure R(A/T)(A)LGX(I/V)(G/T)(N) (SEQ ID NO 39), or expressed as a consensus RXXLGXIXN (SEQ ID NO 53), where X is any amino acid and amino acids in parentheses occur in more than 50% of known destruction sequences.

Examples of other ubiquitination recognition elements are;

KEFAVPNETSDSGFISGPQSS (cactus) (SEQ ID NO 40),
KGPDEAEESQYDSGLESLRSLR (IkBepsilon) (SEQ ID NO 41),
KAADADEWCDSGLGSLGPDA (IkBbeta), (SEQ ID NO 42),
KKERLLDDRHDSGLDSMKDEE (IkBalpha), (SEQ ID NO 43), with a consensus of KX(8–10)DSG (hydrophobic amino acid)XS (SEQ ID NO 44), where the S in bold are phosphorylated. In addition to the signals associated with NF kB activation are the related ubiquitination recognition elements SYLDSGIHSGAT (SEQ ID NO 45), (human beta-catenin) and RAEDSGNESEGE (SEQ ID NO 46), (HIV-1 Vpu) where the S in bold are phosphorylated.

UBIQUITINATION RECOGNITION SIGNAL

Ubiquitination recognition signal is a sequence of a protein which is known to act as the signal for ubiquitination systems. This ubiquitination recognition signal has the ability to promote the ubiquitination of a protein attached directly or indirectly to the signal.

METHOD FOR THE SELECTION OF THE TARGET PROTEIN BINDING ELEMENTS

The subject invention provides a significant advantage over the existing art as it makes use of binding to develop drugs and other compounds with activity against selected target proteins. This advance over the traditional methods is that the invention obviates the need to find a compound which binds to a specific site, by making the whole protein surface available for the development of drugs and other biologically active compounds. This approach thus provides a new avenue for the discovery and selection of novel pharmaceuticals, drugs and other valuable biologically active compounds.

It is understood by those skilled in the art that methods for the discovery of target protein binding elements to a preselected (target) proteins (targets of the subject invention) are well know. Examples are referenced as follows, Karet G, Drug Discovery and Development, January 1999, 32–38, www.rdmad.com/drug; Bohm, H-J and Klebe, G., 1996, Angew. Chem. Int. Ed. Engl. 35, 2588–2614; Angew Chem Int Ed Engl 1996, 35, 2288–2337; Bunin B A., 1996, Methods in Enzymology, 267, 448–465; Patek M., 1995, Tetrahedron Let., 36, 2227–2230; Nestler H P., 1996, Bioorg. Med. Chem. Lett., 6(12), 1327–1330; Look, G C., 1996, Bioorg. Med. Chem. Lett., 6(6), 707–712; Nakayama G R., 1998, Curr. Opin. Drug Discovery and Development 1(1), 85–91; Hill D C., 1998 Curr. Opin. Drug Discovery and Development 1(1), 92–97; Bright, C., 1998, Bioorganic and Med. Chem. Lett. 8, 771–774; Forbes I T., 1998, J Med. Chem. 41(5), 655–657; which are hereby incorporated by reference in their entirety.

The binding molecules of the subject invention are defined by binding to the selected target molecule, having a molecular weight less than 30,000; 50 to 10,000; 50 to 3,000; 50 to 1,000; 100 to 3,000; 200 to 3,000 and 300 to 3,000. Also the binding molecule is defined by the binding affinity which is typically greater than $10^5$ $M^{-1}$. The binding affinity in an advantageous embodiment is greater than $10^6$ $M^{-1}$. The binding affinity in a more advantageous embodiment is greater than $10^7$ $M^{-1}$. The binding affinity in the most advantageous embodiment is greater than $10^8$ $M^{-1}$.

Large libraries of compounds exist in numerous places. These comprise compounds isolated from various natural sources in addition to those generated denovo or partially denovo from natural precursor organic molecules. The sources for various compound libraries include: ArQule (www.arqule.com); Pharmacopeia (www.pharmacopiea); Cerep (www.cerep.com); Merk; Glaxo-Welcome; Zenova; Sigma-Aldrich; Oxford Asymmetry International (www.oai.co.uk); Specs and BioSpecs (www.specs.net); AsInEx (www.asinex.com); ComGenex, Princeton, N.J.; Panax, New York, N.Y.;

Synthetic Approaches for Compound Generation to Screen for Target Protein Binding Elements and Ubiquitination Recognition Elements of the Subject Invention Combinatorial chemistry has been widely adopted by large and small drug discovery companies alike since 1990. This is a set of techniques for creating a multiplicity of compounds and then testing them for activity (Angew Chem Int Ed Engl 1996, 35, 2288–2337). Combinatorial chemistry is used to generate large libraries of molecules instead of synthesizing compounds one by one, as has been done traditionally. These libraries are screened using high-throughput screening to identify the most promising pharmaceutical compounds. Typical rates for success are around 0.1% and libraries of around 200,000 compounds are typically screened. These initial hits in screens are then further analyzed for other desired drug properties for example drug metabolism, bio-availability, stability, potency, and cost. Thus, the discovery of compounds with binding and inhibitory activity is a routine practice. This is especially true if only binding is screened for independent of modulation to the target's activity of interest.

Combinatorial chemistry was first conceived in 1984. Initially, the field focused primarily on the synthesis of peptide and oligonucleotide libraries. In 1984 H. Mario Geysen and his group developed, a technique for synthesizing peptides on pin-shaped solid supports. In 1985, Richard A. Houghten, developed a technique in which tiny mesh packets, act as reaction chambers and filtration devices for solid-phase parallel peptide synthesis.

The field's original predominant focus on peptide and oligonucleotide libraries began to change about 1991 with the development of combinatorial techniques for producing small organic molecules with molecular weights of about 1,000; a class of compounds in which drugs and other valuable bioactive small molecules are most often found.

Two basic methods are used in combinatorial chemistry solid-phase and solution-phase methods. Using these methods combinatorial compounds are created either by solution-phase synthesis or by producing compounds bound covalently to solid-phase particles.

SOLID PHASE METHODS

Solid Phase Methods: (Fruchtel J S., and Jung G., 1996, Angew. Chem. Int. Ed. Engl. 35, 17–42; which is incorporated by reference in its entirety).

Solid-phase synthesis makes it easier to conduct multistep reactions and to drive reactions to completion, because excess reagents can be added and then easily washed away after each reaction step. Another key factor in favor of solid-phase synthesis is that it makes it possible to use split synthesis, a technique developed in 1982. Split synthesis produces large support-bound libraries in which each solid-phase particle holds a single compound, or soluble libraries produced by cleavage of compounds from the solid support. For example in a split synthesis method if you have 3 compound addition steps with 10 compounds used at each step i.e. 10 containers for those compounds. This will generate $10^3$ compounds. Also if you consider all the reaction steps included in a synthesis 10,000 compounds made via a solid phase methods using a three-step chemistry may only require about 22 containers for the chemistry and about 66 liquid handling steps relative to the 10,000 containers and 30,000 liquid handling steps. When you combine these advantages of solid phase synthesis with split synthesis a significant level of synergy is achieved.

A potential disadvantage of solid-phase synthesis is that a hydroxyl, amine, carboxyl, or other polar group are typically present on a molecule to be able to attach it to a solid support. This is a potentially undesirable constraint on the structure of compounds synthesized on solid phase, because products retain the polar group even after they are cleaved from the support. Several groups, have devised traceless linkers that avoid this problem, because the linkers are removed completely from products during the cleavage process. For example, an acylsulfonamide linker that can be displaced by various nucleophiles to add diversity to a library has been described. Another alternative to the traceless linker has been developed using a chemistry, in which reagents used to cleave products from the solid support are incorporated into the product. Using this method a single compound on a solid phase can give rise to a chemical series based on the reagents used to release the products. This can be achieved via the use of substoichiometric amounts of different cleaving reagents, sequentially reacted with a compound that is synthesized on a react-and-release type resin, and each product is individually eluted. This protocol has advantages when combined with automated chemistry systems such as those used for peptide and oligonucleotides synthesis. The number of compounds generated with this method can be up to 10 times the number of chemistries generated on the solid phase. The result is also a relatively pure product in solution. This method is an example of the combinations of solid and solution phase chemistries.

In order to solve one of the problems caused by the use of split synthesis methods, namely knowing which compound in the library shows activity, encoded libraries have been constructed. An example of an encoding technique is one based on inert halogenated compounds that are used to record the chemical reaction history of each support bead. The tags can be analyzed by capillary gas chromatography with electron capture detectors and autosamplers to rapidly reveal the identity of active compounds in the library. In addition to this method compounds can be released from the bead and analyzed by MS and/or GC/MS. Other alternatives to the deconvolution of the library are based on the resynthesis of sub set pools from a positive hit of pooled compounds. One exciting approach to this problem of compound identification (from a screen of pooled compounds), is based on the use of affinity selection plus size exclusion chromatography (to separate bound compounds from those that have little or no affinity for the target protein), followed by mass spectroscopy, to identify leads that bind to the target of interest. This method eliminates the need to encode the library and makes use of the molecular weight of the compound as the tag. Some problems may be encountered from redundancy of some molecular weights within a library, but higher resolution and fragmentation MS methods can be used effectively. In addition combinations of these approaches can be considered where the tag is left attached to the compounds which bind to the target molecule of interest and are then selectively eluted and subjected to cleavage releasing the tag or code which can then be identified by MS or GC/MS methods (Karet G, Drug Discovery and Development, January 1999, 32–38, www.rdmad.com/drug; which is here by incorporated by reference in its entirety)

SOLUTION PHASE METHODS

Solution phase chemistry is favored by many for library construction due to the wider range of organic reactions available for solution-phase synthesis, the technology used traditionally by most synthetic organic chemists, and products in solution can be more easily identified in standard drug target assays and characterized. A problem for solution-phase synthesis of one molecule at a time is the final purification that can be both expensive and slow. Chromatography is commonly a first resort since it usually works. In addition, the problems associated with solution chemistry are compounded when attempting to make tens of thousands of compounds to generate a library or a 'book' for a library.

In the generation of libraries of chemistries numerous methods have been devised resulting in the wide spread use of large libraries of chemicals to readily allow the discovery of potential drug candidates. The generation of chemical libraries that are free in solution is typically the goal of most of the pharmaceutical industry. This aim is due to the nature of many of the drug targets and the associated assays. Also the construction and utility of chemical libraries is typically facilitated but the generation of master plates of compounds in solution to form the basis of the chemical library. Thus the general advantages of the solid phase synthesis methods are typically not fully realized in the context of the current drug discovery efforts. The main reason for this is the interest not in binding of the compound to the drug target but to demonstrate that the activity of the drug target is altered, which typically requires compound free in solution. Further concerns with libraries of compounds on a solid phase arise from concerns of the potential influence of the linker and steric effects on the compounds bound to the solid phase.

Thus methods for the discovery of compounds which bind to target molecules is known in the art. Also, the optimization of the initially discovered compound is well known in the art where the affinity is improved by generation of a pool of related compound via a more selective combinatorial chemistry approach.

The present invention provides a mechanism to overcome these problems in drug and small molecule discovery.

EMBODIMENTS OF THE SUBJECT INVENTION

Compounds Active on 5-Lipoxygenase as Anti-Asthmatics

Screening for Target Protein Binding Elements

Initially a target protein is selected, for example 5-lipoxygenase which is a molecule involved in inflammatory reactions especially in asthma. Target protein for the subject invention come from numerous fields where small molecules are used to achieve modulation of a biological system in eukaryotic organisms. Examples of such fields are insecticides, fungicides, antivirals, herbicides, anti-parasitics and herbicides when applied to humans, animals and plants.

The target protein is then either purified from a natural source in order to provide sufficient material for the screen or expressed via recombinant methods to provide sufficient material for the screens.

The target protein is then either labeled directly with a detectable species such as a radioactive, electrochemiluminescent, and chemiluminescent or fluorescent label or with an indirectly detectable species such as an enzyme, or particle. Alternatively an antibody or equivalent with binding activity to the 5-lipoxygenase is labeled.

The next step is to buy a library of compounds for screening. A library of from 1,000 to 1,000,000 is typical of the size that is screened. These are available from a series of companies as described earlier. These libraries of compounds are used to screen for the binding of the target protein 5-lipoxygenase. Ideally compounds are bought still bound to the solid phase or are screened for binding directly to immobilized target protein 5-lipoxygenase using methods as described below for screening.

It is also possible to generate a chemical library of various potential binding molecules bound to a solid phase following conventional methods to give rise to differing potential compounds. The optimal methods for the construction of the chemical library is to employ the methods of split synthesis coupled to the solid phase (as outlined above). The library is generated using a series of solid phase chemistries such as to give rise to various 'chemical books' that in compilation form the basis of a library. The library is screened in the form of a library or in the form of the 'chemical books'. Typically one would take the products from the split synthesis and pool the solid phase and use this as the basis for the screen.

To the pool of beads used as the solid phase for the synthesis, a mixture of buffer, detergents, salts and blocking agents such as serum albumin or other proteins are added. This buffer addition step is used to 'block' the beads or solid phase in such a way that any significant non specific binding of the selected target (5-lipoxygenase) does not occur. Following this blocking step the beads are washed and followed by the addition of the 5-lipoxygenase either labeled or not. The beads or solid phase are then incubated to allow the binding of the target protein binding elements to the target, in this case 5-lipoxygenase. Following the incubation of the target molecule to the beads or solid phase the beads are washed and then the binding of the labeled 5-lipoxygenase detected directly. In an alternative format, if the 5-lipoxygenase is labeled with an indirectly detectable label such as an enzyme, the beads are then placed in to a substrate reaction solution to detect the presence of the enzyme label. In the case of an enzyme label, substrates for these detection methods are based on insoluble chromogenic products. In the case where the 5-lipoxygenase is not labeled and an antibody or equivalent is available, the beads are subjected to another binding reaction where the antibody or equivalent, is labeled either directly or indirectly as suggested for the labeling of 5-lipoxygenase. It is also possible at this step to not use a labeled antibody or equivalent and to add a further step where the labeled antibody or equivalent is used. These additional steps can be detected using the same standard methods known in the art as suggested for the directly labeled 5-lipoxygenase.

Following these steps a series of beads are identified and these beads are selected from the bead population and subject to analysis to determine the structure of the binding molecule that is able to bind the 5-lipoxygenase as in this example. This is achieved by the use of GC/MS or via molecular tags used during the construction of the library as described earlier. Alternatively a pool which was positive is re-made generating a series of sub pools for screening and further re-synthesis and dividing out of the various pooled compounds until a single compound is presented in a single well for analysis allowing the determination of the active compound.

Addition of the Ubiquitination Recognition Element

At this point in the compound discovery path for the subject invention, the target protein-binding element of the compounds of the invention has been identified. These optimal binding molecules are then subjected to further chemistry to add the ubiquitination recognition element.

An alternative approach to the discovery of the target protein-binding element is based on solution phase screening. In such an example compounds (available either via synthesis, natural products or from companies such as ArQule (www.arqule.com), Pharmacopeia (www.pharmacopiea), and Cerep (www.cerep.com) are obtained and added to the target protein of interest and then subjected to size exclusion to remove the unbound compounds. The protein bound fraction is then subjected to GC/MS to identify the molecules. In this way the solution phase screening is made rapid and facile for compounds in solution.

Compounds Active on IL-4 Receptor as Anti-asthmatics
Introduction

A further embodiment of the subject invention is the development of a compound targeted to a receptor involved in development of asthma. In recent studies into the pathophysiology of asthma, IL-13 has been demonstrated to be the central mediator acting through the IL-4 receptor. Thus asthma can be controlled by the lowering of either the IL-13 or IL-4 receptor. The IL-4 receptor consists of two subunits; a 140kd alpha subunit, which binds IL-4 or IL-13 and transduces their growth-promoting and transcription activating functions and a gamma c subunit, common to several cytokine receptors, which amplifies signaling of IL-4 receptor alpha. In this application of the subject invention the target for drug development is the IL-4 receptor alpha chain. The IL-4 receptor alpha chain has a large intra cellular protein domain that forms the specific molecular target of the discovery approach of the subject invention.

Expression of the IL-4 Receptor Alpha Chain

Initially the IL4 receptor alpha (IL-4a) chain intra-cellular domain is cloned from human blood lymphocytes. The cloned DNA is engineered to generate a gene sequence that directs the expression of the cytoplasmic domain of the IL-4a chain. This gene sequence is also engineered to include a sequence tag that allows the purification and detection of the expressed receptor sub-unit. This expression is carried out using various methods known in the art. Methods for expression of proteins, are numerous; an example of one is one of the vectors from Invitrogen (Carlsbad, Calif.) such as the His-Patch ThioFusion, which allows for the optimal expression of proteins in a soluble form and containing a His tag which allows rapid purification. This system allows for the production of soluble protein after cleavage using the enterokinase cleavage site in the cloning vector pThioHis A, B, C. An alternative Xpress system also provides a useful expression system which allows rapid purification via a His sequence and also a protease cleavage site to yield the protein of interest with out the His sequences. One of the vectors from the Xpress system, pTrcHis2 A, B, C series is especially useful; this vector allows the use of the His sequence for purification but also allows for the tagging of the protein with a myc epitope for detection and assays for the expressed protein containing the epitope tag sequence myc with an anti-myc antibody.

Expression vectors are also supplied by other vendors such as New England Biolabs (Beverly, Mass.) whose pMAL-c2 and pMAL-p2 vectors provide an expression system for E.coli which provides a tag which is maltose binding protein (MBP), this tag can be used in purification and also in detection of the fusion protein. The MBP can be removed by the use of the factor Xa cleavage site.

Following the cloning of the IL-4a cytoplasmic domain, using art known methods for the cloning and expression of proteins, the recombinant protein is expressed and purified using the tag sequence attached during the cloning. This purified receptor sub-unit is then subjected to screening against a chemical library.

Screening for Binding Molecules from Chemical Libraries

The step of screening for specific molecules is made easy in this invention as only binding activity is desired and not specific modulation of the target protein as is required in traditional drug discovery.

The next step is to buy a library of compounds for screening. A library of from 1,000 to 1,000,000 is typical of the size that might be screened. These are available from a series of companies as described earlier. These libraries of compounds are used to screen for the binding of the target protein 5-lipoxygenase. Ideally compounds are bought still bound to the solid phase or are screened for binding directly to immobilized target protein 5-lipoxygenasen using methods as described below for screening.

It is also possible to generate a library of from 1,000 to 100,000 compounds contained on a solid phase using split synthesis methods as described earlier. This library is constructed using a series of chemical methods resulting in pools of the solid phase used during synthesis which form the basis of the 'books' which go to make up the library. In addition at the final chemical coupling step used to construct the various books the solid phase pools are stored in subpools forming 'chapters' of the 'books' in the libraries. These so called 'chapters' form the basis for screening as they contain not only pools of compounds but also a known chemical-coupling step used in the synthesis of the 'chapters' of the library.

The library can then be screened using two approaches. In both cases the solid phase from the chemical library to be screened is subjected incubation with assay buffers with blocking agents such as for example; proteins (i.e. BSA, gelatin), polyvinylpyrrolidone, ficoll, heparin, detergents (i.e. SDS, Tween, NP40, Triton X-100). This incubation step is to block the non-specific binding sites on the solid phase used in the generation of the library and allow the determination of specific binding events. This initial incubation is an art recognized step in various binding assays such as ELISA, southerns, westerns etc. Following this incubation with blocking agents the protein of interest is then added to a buffer which typically has the same composition as that during the blocking step but can also be modified using lower or no additional blocking agents with the exception of the detergents which are typically always present during a binding reaction.

In one of the screening methods the 'chapters' of the various 'books' following the blocking step are then subjected to binding with the purified receptor sub-unit. The solid phase from this incubation is then washed and subjected to a second binding step with a labeled reagent which binds to the tag sequence added to the receptor sub-unit during the recombinant engineering for the expression of the receptor sub-unit. Typically an antibody to this tag recognizes the tag sequence; examples that are in common use are the myc, flag, and his epitopes. Following the incubation with the tag specific binding species the presence of the labeled binding species is detected by the presence of the label that is typically an enzyme such as alkaline phosphatase or peroxidase. The detection step typically makes use of an insoluble chromogenic substrate that is readily detected by eye or by image analysis systems.

In an alternative method soluble substrates can also be used and screened using ELISA plate readers, eye or other spectrophotometric methods. In its simplest form the various 'chapters' of the 'book' from the library are screened by eye to look for beads that have developed a color due to the enzymatic action on the chromogenic substrate. These colored beads indicate that the receptor sub-unit is binding to one of the compounds within the 'chapter' the next step is to determine if these so called positive 'chapters' contain specific binding or if binding is just to the tag binding reagent or some non-specific activation of the chromogenic substrate. To achieve this, the positive 'chapters' are screened with out the specific binding step to the receptor sub-unit. If these positive 'chapters' now become negative or show significantly reduced signals interms of positive solid phases with in the mixture then these are considered to be real positive hits in the screen. These real positive 'chapters' are then subjected to re-synthesis. In this re-synthesis the initial chemical steps to create the specific binding molecule is unknown only the last chemical coupling step in the compound synthesis is know, as this formed the last chemical step which constructed the 'chapter'. During the re-synthesis of the positive chapter the chemical step prior to the last chemical coupling is carried out as in the initial synthesis but the solid phase is not pooled and split for the final chemical coupling but are maintained as separate pools then subjected to the chemical coupling step know for that chapter. This re-synthesis results in the formation of a new series of solid phase compound pools which have the last two chemical coupling steps known. This new series of solid phase compound pools are screened as in the initial screen and positive pools are checked as previously for the binding specificity to identify positive pools. The positive pool(s) now allow the re-synthesis of the pool(s) with the last two steps for the generation of the compound which specifically binds to the receptor sub-unit. The positive pools are then subjected to the same cycle of re-synthesis and screening as just described but with the last two chemical coupling steps know the pools are maintained individually prior to the last know step. In this way the synthesis of the specific compound able to bind to the receptor sub-unit is deconvoluted from the chemical 'library' and identified.

In an alternative method the positive solid phase is removed from the screen and collected. These are then subjected to the cleavage reaction which removed the specific chemistry from the solid phase followed by the analysis of the various chemical species using GC to separate the individual compounds followed by MS to determine the molecular weight. This information coupled with the synthesis methods used is used to determine the compound identity. After the determination of these various candidate specific binding molecules they are then re-synthesized and subjected to the binding assay to check if these are the specific compounds that resulted in the positive solid phases.

Addition of the Ubiquitination Recognition Element

This screening effort following methods and protocols known in the art allows the identification of compounds that bind to the receptor sub-unit. These compounds then form the basis for the development of compounds of the invention. These compounds are then subjected to further chemistry based on the use of the linker group used in the development of the solid phase chemistry. To this linker group the various ubiquitination recognition chemistries are added. This final step of chemistry generates the compound of the invention. The compound of the invention are then subject to analysis to determine which of the compounds from the chemical library screen with which of the ubiquitination recognition elements is able to function most effectively in the targeted ubiquitination and/or degradation. In the case where the ubiquitination recognition chemistry is based on the N-end rule the rabbit reticulocyte lysate forms the basis for the assay using the recombinant produced receptor sub-unit labeled with for example $^{125}$I to follow the fate of the protein. In addition the compounds of the invention can be tested in a mammalian tissue culture system where the target protein either intact or as an engineered fragment is expressed. In such a mammalian tissue culture system the compounds effect on the target protein's level is determined by making use of the tag sequence which can be engineered into the recombinant expression of the target protein during the construction of the mammalian tissue culture test system. The tag sequence is used to determine the levels of the target protein during the incubation with the potential compounds screened and synthesized as described above. This assay for the tag sequence can take the form of a western blot or via an ELISA, for example. Other tags which are valuable to use are those based on the green fluorescent protein, which allows the analysis of protein levels in living cells and/or organisms.

The compounds that show the optimal activity in the test systems will then form the basis for the next stage of drug development. In this next stage these selected compounds are subjected to the recognized drug development path. The drug development path determines the potential value of the compounds by evaluating a series of factors including bioavailability; toxicology, pharmacology and efficacy in animal models before the compounds are considered for human testing.

Development of Pesticides

An alternative embodiment of the subject invention is the development of pesticides. Pesticide is a general classification that includes insecticides, rodenticides, fungicides, herbicides, and fumigants. The aim of the pesticide is the destruction of some life form and as such selectivity is desirable. The methods that have been described for the subject invention for development of active compounds to the 5-lipoxygenase and IL-4 Ra also apply to the development of pesticides. Pesticides are also compounds of the invention, which are targeted to an important biochemical pathway in a pest that is required for its survival or prolonged viability. A pest is an organism that has some direct or indirect deleterious effect on mankind. The term pest is widely used to cover any organism that has some direct or indirect deleterious effect on mankind. Some examples of pests are aphids, moths, lice, fleas, locusts, mice, rats, weeds etc. In the development of a pesticide the methods outlined above are followed with the exception of the target in the case of developing pesticides key biochemical pathways for survival in the pest would form the basis of the molecular target selected to screen for protein binding elements. In the case of insecticides examples of key biochemical pathways include, ecdysone 20-monooxygenase, ion channel of the GABA gated chloride channel, acetylcholinesterase, voltage-sensitive sodium channel protein, calcium release channel, and chloride channels.

The subject invention is ideally suited to the optimal development of pesticides due to subject inventions ability to rapidly screen for specific interactions which can be developed into a highly species specific compounds of the invention. Specificity is of prime importance for the development of pesticides as the targeted pests are either present in close proximity to mankind, or as in the case of agriculture pests, the pests are targeted on food intended for mankind where toxic compound residues are unacceptable. For example, in the case of pesticides that are targeted to kill aphids, the compound is ideally targeted only to the aphids and has no effect on the beneficial insects such as ladybugs, and bees. The subject invention provides through its molecular basis of compound selection, both a facile and an improved method for the development of pesticides. In the development of an optimal pesticide the specific target protein involved in the key biochemical pathway is cloned and engineered using well known methods to generate a source of protein for screening the chemical compound library which has sequence tags to enhance the screening and characterization of the compounds of the invention. This process is also repeated using the proteins from the organisms also posses the same critical biochemical pathways but are not the target pests. Thus a set of proteins can be developed from the pest organism and from organisms which are likely to be exposed to the compounds of the invention when used as pesticides. In the screening procedures as described earlier for the development of the anti-asthmatic compounds in addition to the screen for binding to the desired target, absence of binding can also be screened for using the proteins from the non-pest organisms. In this way a set of compounds can be selected which show specificity to the target pest organism and not commonly encountered or related non-pest organisms. This type of screening is an advantage of the subject invention as it is based on the use binding and does not require a complex activity assay. In this way the subject invention provides for a low cost and rapid route to the selection of molecular species which have a high degree of species specificity.

The subject invention allows for the development of selective pesticides. The development of pesticides follows many of the previously described methods. The screen methods for the binding molecules that recognize the specific target have been described earlier for the IL-4 receptor alpha chain and 5-lipoxygenase. These screens are used in order to find molecules with the binding affinity for the target proteins of interest; for example to develop a specific herbicide the protein enolpyruvylshikimate-phosphate synthase represents a good target as this is the molecular target for glyphosate. The target protein is either purified from the natural source or cloned and expressed using various recombinant methods to produce the enolpyruvylshikimate-phosphate synthase. An ideal target for the development of a selective herbicide is poison ivy, in this case the enolpyruvylshikimate-phosphate synthase from poison ivy is used as the source of the target protein. The screen for the binding molecules is initially focused on this target but secondary screens are carried out on the various other plants enolpyruvylshikimate-phosphate synthase normally present in the same environment as poison ivy is found growing naturally. The secondary screen is used to establish the binding molecules that do not bind to the other plant enolpyruvylshikimate-phosphate synthases in order to provide the level of specificity desired. Following the identification of the selective binding molecule this is then coupled to the ubiquitination recognition element in order to generate the herbicide of the subject invention, which is selective to poison ivy. The development of the selectivity is further enhanced using comparative sequencing of the various molecular targets thus defining the various sequence elements that are unique to poison ivy (or other target organism). The sequence information then allows both the definition of the molecular binding site within the molecule but also the sequences of the various proteins that are used in the secondary screens to define the specificity of the final binding molecules from the screen. It will be understood that the methods described in the subject invention benefit greatly from the recent advances in genomic sequencing which make much of the sequence information readily available or easily obtainable. It will be understood by those skilled in the art that these methods can be applied readily to any pest in the development of pesticides. In the case where no molecular target is known or can be defined it will be understood that the subject invention also allows a route to discovery of such molecular targets. This discovery can be achieved through the selection of targets by various levels of homology with know targets or via selection based on no homology which leads more rapidly to the development of selectivity even if it takes longer to define the role and value of these new molecular targets. Other examples of targets for the development of herbicides include, Acetyl-CoA carboxylase, adenylosuccinate synthetase, protoporphyrinogen oxidase, and enolpyruvylshikimate-phosphate synthase.

Development of Compounds Effective Against Parasites

In the development of compounds that are targeted to parasitic organisms the current invention provides for significant advantages. It has been traditionally a problem developing drugs that provide for the selective toxicity to various parasites of mankind and his domestic animals. This problem has been largely due to the problems of culturing these organisms and to the problems of finding a toxin that has the desired level of toxicity to the parasite with out damaging the host organism. This problem has presented itself due to the large number of related biochemical pathways that are shared between the eukaryotic organisms. Some efforts have been made with some success to define biochemical differences this has not yielded a broad range of targets for the development of drugs. The subject invention provides for a more facile and optimal method for the development of compounds effective against parasites in the groups of Protozoan parasites: Balantidium, Cryptosporidium spp., Giardia spp, Plasmodia, Trypanosoma, Leishmania, Trichomonas, Entamoeba, Eimeria, Toxoplasma, Plasmodium, Babesia, Theileria, Metazoan parasites: Nematode parasites, Ascaris spp., Capillaria spp., Dracunclus spp., Enterobius spp., Filariasis due to various organisms, hookworm infections, Strongyloides spp., Toxocara spp., Trichinella spp., Trichuris spp., Taenia spp., Diphyllobothrium spp., Hymenolepis spp., Echinococcus spp., Shistosoma spp., Fasciolopsis spp., Heterophyes spp., Metagonimus spp., Clonorchis spp., Opisthorchis spp., Paragonimus spp. etc.

Targets for compound development: Leishmania, proteins of the sterol synthesis pathway: Plasmodium, dihydrofolate reductase; dihydrofolate reductase-thymidylate synthase (bifunctional) resistance known due to mutations in the gene for this enzyme, heme polymerase: Trypanosoma, ornithine decarboxylase, trypanothione reductase, Ornithine decarboxylase of the trypanosoma represents an desirable candidate for destruction due to its long half-life and low turn over in trypanosoma.

Protein Level Control

This invention is also to a method for the control of protein levels with a cell. This is based on the use of compounds of the invention which are known to interact with a specific protein or protein sequence element. These specific proteins known to interact with compounds of the invention are used to generate chimeric fusion proteins with a desired target protein. These chimeric fusion proteins thus functionally link the ability to be destabilized by the compounds of the inventions to the desired target protein. In this way known compounds of the invention and known proteins and/or protein sequence elements can be combined to target the genetic engineering of another protein to render it degradable and thus controllable by a compound of the invention. The following are by way of illustration of some possible application of this idea.

Control of Protein Levels Within a Cell

In another embodiment of the subject invention, control of specific gene products is achieved. In this embodiment a gene(s) is engineered such that its expression results in the production of the desired protein but with the addition of a protein which has a specific binding affinity for a small molecule. Examples of such sequences are streptavidin, avidin, antibodies, single chain antibodies, thioredoxin, maltose binding protein, and the peptide motif CCXXCC (SEQ ID NO 47), and WEAAAREACCRECCARA (SEQ ID NO 48), (Griffin B A, 1998, Science 218, 269). In the case of thioredoxin and the peptide motif CCXXCC (SEQ ID NO 47), WEAAAREACCRECCARA (SEQ ID NO 48), and AEAAAREACCRECCARA (SEQ ID NO 49), these are known to bind to tightly to organoarsenical compounds. One potential binding species for the peptide motif CCXXCC (SEQ ID N:47) and WEAAAREACCRECCARA (SEQ ID NO 48), and AEAAAREACCRECCARA (SEQ ID NO 49), is 4',5'-bis(1,3,2-dithioarsolan-2-yl)fluorescein with other bis-organoarsenical being useful (Griffin B A, 1998, Science 218, 269, which is hereby incorporated by reference in its entirety).

Having generated the modified gene for the protein of interest these genes are then introduced into the cells desired either forming the basis of a cell culture study in vitro or through the generation of a transgenic animal which expressed the modified gene in its normal context or aberrantly to determine its role within the intact organism. An example of this type of engineering is described in Griffin B A, 1998, Science 218, 269.

In this embodiment the compound of the invention is built around the small molecule with a specific binding affinity for a specific amino acid as exampled above. In the above example these are biotin binding with streptavidin and avidin, any small molecules binding with single chain antibodies such as biotin, digoxin, fluorescein and the organoarsenical compounds such as 4',5'-bis(1,3,2-dithioarsolan-2-yl)fluorescein, p-aminophenylarsine oxide binding with thioredoxin and the peptide motif CCXXCC (SEQ ID NO 47), WEAAAREACCRECCARA (SEQ ID NO 48), and AEAAAREACCRECCARA(SEQ ID NO 49). To these binding molecules are attached the ubiquitination recognition elements to generate a bifunctional molecule which is able to bind to the genetically engineered protein and activate the ubiquitination of the engineered protein. Having generated these bifunctional molecules these then are used to treat the cells and/or organisms which contain the engineered protein. This treatment results in the rapid degradation of the engineered protein in a dose dependent fashion allowing the determination of the role of the various proteins in the biology and/or physiology of the cell and/or organism. This embodiment of the subject invention allows the rapid generation of a series of mutant proteins, making use of an identical compound and treatment schedule in affecting changes within a cell and/or an organism that allows for optimal determination of the role of various proteins in an controlled study. This is achieved with less perturbation of the cell and/or organisms natural biochemistry than is possible with other methods.

Control of Green Fluorescent Protein Levels

An example of the above embodiment is directed to the demonstration of targeted ubiquitination to mediate degradation of a protein inside living cells. The green fluorescent protein (GFP) ECFP plasmid vector (Clontech, Palo Alto, Calif.) was chosen in order to engineer the following binding site AEAAAREACCRECCARA (SEQ ID NO 49), into the C terminus of the expressed ECFP (GFP) following established methods to form an expression vector able to direct the expression a GFP with a C terminal tagged end ECFP-Cys4 (Griffin B A, et al 1998 Science, 281, 269–272). This choice of the ECFP was also made so that the formation of the complex of 4',5'-bis(1,3,2-dithioarsolan-2-yl)fluorescein with the ECFP-Cys4 demonstrates fluorescent energy transfer (FRET) from ECFP-Cys4 to the bound 4',5'-bis(1,3,2-dithioarsolan-2-yl)fluorescein. This vector with the ECFP-Cys4 gene is then transfected into HeLa cells and demonstrates that expression is obtained and the protein had the expected long half life of >20 hrs. Various compounds of the invention are made as follows; with 4',5'-bis(1,3,2-dithioarsolan-2-yl)fluorescein coupled using EDC chemistry, to a ubiquitin recognition elements selected from Arg-εAhx-Lys; Arg-β-Ala-εAhx-Lys; Arg-εAhx-εAhx-Lys; Phe-εAhx-Lys; Phe-β-Ala-εAhx-Lys; Phe-εAhx-εAhx-Lys, or p-aminophenylarsine oxide coupled using EDC chemistry, to a ubiquitin recognition elements selected from Arg-εAhx-Ala; Arg-β-Ala-εAhx-Ala; Arg-εAhx-εAhx-Ala; Phe-εAhx-Ala; Phe-β-Ala-εAhx-Ala; Phe-εAhx-εAhx-Ala. These compounds of the invention molecules are then added to the cells transfected with the ECFP-Cys4 expression vector and subsequently treated with 100 ug/ml cycloheximide to block further protein synthesis. The fluorescence is measured over time to determine the levels of the protein and the protein bound to the compounds of the invention, using excitation at 440 nm and emission at 480 nm to look at ECFP levels and 635 nm when the 4',5'-bis(1,3,2-dithioarsolan-2-yl)fluorescein based compounds are used. The stimulation of degradation seen with the p-aminophenylarsine oxide based compounds was observed by drop in fluorescence of the ECFP relative to control cells. In the case of the studies with the 4',5'-bis(1,3,2-dithioarsolan-2-yl)fluorescein based compounds an initial rise of the FRET signal at 635 nm is seen followed by a drop in the signal compared to controls where only 4',5'-bis(1,3,2-dithioarsolan-2-yl)fluorescein is used to treat the cells. In addition to these fluorescence studies, the levels of protein using western blot analysis is examined using an antibody to the ECFP, GFP (Clontech, Palo Alto, Calif.), which demonstrated that compounds of the invention lower the levels of the ECFP. Concentrations for the various compounds and other molecules used were from 0.1 uM to 100 uM. This study showed the ability to use the targeted ubiquitination to alter the levels and half-life of a protein in a living cell using compounds of the invention.

Control of Protein Levels in the Liver of a Transgenic Organism

An example of the above embodiment is the demonstration of targeted ubiquitination to mediate quantitative and tissue specific control of gene expression in transgenic mice. The expression vector was constructed using the luciferase gene and a liver specific promoter $P_{LAP}$, the promoter of the liver-enriched activator protein driving the expression of the luciferase gene (Kistner A., 1996, Proc. Natl. Acad. Sci. 93, 10933–10938). The luciferase gene was engineered to contain the AEAAAREACCRECCARA (SEQ ID NO 49), sequence at the C terminus using synthetic oligonucleotides and PCR based cloning. The final expression vector consisted of the $P_{LAP}$, promoter driving the expression of the luciferase gene containing the AEAAAREACCRECCARA (SEQ ID NO 49), sequence (the binding site for the compounds of the invention). This expression vector was then used to generate transgenic mice. Transgenic mice lines were generated by pronuclear injection using standard techniques and analyzed by Southern blot using a BamHI-EcoRV fragment of the luciferase gene (Kistner A., 1996, Proc. Natl. Acad. Sci. 93, 10933–10938). The tissue specific expression of the modified luciferase gene was demonstrated using standard methods on liver, pancreas, kidney, stomach, muscle, thymus, heart, and tongue. In order to modulate the levels of the luciferase gene the transgenic mice were injected with 4',5'-bis(1,3,2-dithioarsolan-2-yl)fluorescein coupled using EDC chemistry, to a ubiquitin recognition elements selected from Arg-εAhx-Lys; Arg-β-Ala-εAhx-Lys; Arg-εAhx-εAhx-Lys; Phe-εAhx-Lys; Phe-β-Ala-εAhx-Lys; Phe-εAhx-εAhx-Lys, or p-aminophenylarsine oxide coupled using EDC chemistry, to a ubiquitin recognition elements selected from Arg-εAhx-Ala; Arg-β-Ala-εAhx-Ala; Arg-εAhx-εAhx-Ala; Phe-εAhx-Ala; Phe-β-Ala-εAhx-Ala; Phe-εAhx-εAhx-Ala, which formed a set of compounds of the invention. The serum concentrations achieved are from 1 micromolar to 1 millimolar. The levels of luciferase activity are lowered as the doses of the various compounds are increased. This response was also seen when the study was carried out using liver slices invitro using similar concentrations in the tissue culture medium used for the liver slice incubations.

Control of the Physiology a Transgenic Organism

An example of the above embodiment is the analysis of the effect of expressing CaMKII on specific forms of memory. CaMKII is a serine-threonine protein kinase expressed primarily in neurons of the forebrain. The ability of CaMKII to become persistently active in response to a transient Ca stimulus indicates its potential involvement in memory. Mutation of the Thr286 to Asp in CaMKII (CaMKII-Asp286) produces a calcium-independent form that mimics the auto-phosphorylated form. The transgenic expression of CaMKII-Asp286 leads to a shift in response to stimulation as well as a severe defect in spatial memory. To obtain tissue-specific and ubiquitin regulated degradation a line of mice is generated expressing the CaMKII-Asp286 tagged with a AEAAAREACCRECCARA (SEQ ID NO 49), sequence (CaMKII-Asp286-tag) under control of the native CaMKII promoter to ensure natural tissue specific expression. In addition a line of mice was also constructed expressing beta-galactosidase tagged with a AEAAAREAC-CRECCARA (SEQ ID NO 49), sequence (beta-gal-tag) under control of the native CaMKII promoter. These mice both demonstrated forebrain-specific expression. Severe defects in spatial memory were observed in response to CaMKII-Asp286-tag expression using the Barnes circular maze. The treatment of these mice brains with the 4',5'-bis(1,3,2-dithioarsolan-2-yl)fluorescein, p-aminophenylarsine oxide coupled to a ubiquitin recognition elements selected from Arg-εAhx-Cys; Arg-β-Ala-εAhx-Cys; Arg-εAhx-εAhx-Cys; Phe-εAhx-Cys; Phe-β-Ala-εAhx-Cys; Phe-εAhx-εAhx-Cys, demonstrated a reversal of this profound memory impairment. In the mice with the beta-gal-tag expression treatment of both the mice and tissues from the fore-brain with 4',5'-bis(1,3,2-dithioarsolan-2-yl) fluorescein, p-aminophenylarsine oxide coupled to a ubiquitin recognition elements selected from Arg-εAhx-Cys; Arg-β-Ala-εAhx-Cys; Arg-εAhx-εAhx-Cys; Phe-εAhx-Cys; Phe-β-Ala-εAhx-Cys; Phe-εAhx-εAhx-Cys, demonstrated dramatic reductions in the levels of beta-galactosidase activity. This system has the distinct advantage over the currently available systems which are based on multiple gene products, unnatural and modified promoter elements, requiring multiple rounds of transfection and the screening of multiple clonal cell lines to identify the desired cell line from each transfection; for example the Tet-Off™ and the Tet-On™ gene expression system (U.S. Pat. No. 5,464,758) sold by Clontech (Palo Alto, Calif.; www.clontech.com).

Control of Gene Expression

In an extension of the above embodiments, relating to the control of gene expression. The tag sequence or its equivalent can be genetically engineered into the coding sequence of various transcription and/or transactivating factors to render their protein levels within the cell sensitive to the presence of a small molecule activator of the ubiquitination pathway. In this way any given transactivating factor (X) can be modified to contain tag sequence as above resulting in the expression either in the native tissue or other-wise via the modification of said transactivating factors promoter and/or operator and/or enhancer region, to allow the expression of X-tag. The levels of the X-tag protein can then be controlled via the use of a small molecule activator of the ubiquitination pathway in order to affect the expression of any given gene dependent on said X for control and thus its protein product, in order to determine its role or to control some other aspect of the cell or organisms biochemistry, physiology or form though the modification of gene expression. An example is a transactivating factor that controls multiple proteins expression levels. Control of this single transactivating factor results in the effective control of multiple proteins via a small molecule activator of the ubiquitination pathway.

Control of Steroid Production in Genetically Engineered Animals

A ramification of the proceeding embodiment is the possibility of generating modified cells and organisms which contain either a single protein or multiple proteins modified with a selective binding domain which allows the control of a specific gene with the cells or organisms to give rise to a desired biological effect. For example the reduction of boar taint in pigs can be achieved by the removal of the hormone GnRH. This embodiment of the subject invention allows for the modification of the GnRH receptor to allow its targeted degradation in the presence of a compound of the invention. In this way boar taint can be controlled by feeding a compound of the invention, that down regulates the receptor resulting in the reduction of steroid biosynthesis responsible for boar taint.

Control of Flower Color in Genetically Engineered Plants

In a further example, a gene for the biosynthesis of a flower color is modified, allowing expression of a functional protein tagged with the specific binding sequence. This expression of a modified protein involved in the biosynthesis of flower color, such as the genes involved in the biosynthesis of flavonoids, carotenoids and anthocyanins; i.e. flavanone 3-hydroxylase, anthocyanin synthase, dihydroflavonol 4-reductase, flavonoid 3',5'-hydroxylase, anthocyanin 5-aromatic acyltransferase, UDP-glucose:flavonoid 3-O-glucosyltransferase, anthocyanin rhamnosyltransferase, anthocyanin 3'-methyltransferase, anthocyanin 3'5'-methyltransferase, leucoanthocyanidin dioxygenase, anthocyanidin synthase, anthocyanin acyltransferase, chalcone synthase, chalcone flavanone isomerase, glutathione S-transferase, allows for the modification of flower color by addition of the compounds of the invention specific for the modified biosynthetic protein. In addition to the proteins involved in the synthesis of flower color, the gene products involved in the regulation of the expression of the synthases and other proteins involved in the production of flower color are also considered targets of the subject invention. Examples of the regulatory genes include the R and C1 gene families, an2 and jaf13, the delila gene. Quattrocchio F. 1998, Plant J. 13(4), 475–488.

Resistance Control in Genetically Engineered Plants

In a still further example of the above embodiment of the subject invention relating to the selective control of protein levels to achieve a desired biological response. The gene involved in the herbicide resistance to glyphosate (Roundup®) in Roundup Ready® soybeans the enolpyruvylshikimate-phosphate synthase from the bacteria agrobacterium sp. Strain CP4 (CP4EPSPS), is engineered with a gene sequence encoding a small molecule binding sequence i.e. tag as described above, which allows the activation of the targeted degradation of the herbicide resistance marker using compounds of the invention. In this way transgenic plants containing the engineered resistance gene CP4EPSPS can be rendered sensitive to the herbicide glyphosate by contacting the transgenic plants with compounds of the invention.

Gene Expression Control in Gene Therapy Vectors

In a further example of the selective control of protein levels it is contemplated that the genes for pre-selected proteins are engineered to contain the coding sequence for a small molecules binding sequence. Thus rendering the protein, expressed from the engineered genes of the pre-selected amino acid, targets for compounds of the invention that allows these proteins activity and/or levels to be controlled by the compounds of the invention. The engineered genes of the pre-selected amino acid are then cloned into vectors for gene transfer into a host.

In the case of human gene therapy vectors that are useful are viruses such as; adenovirus, retroviruses, herpes virus, vaccina virus. In the case of other organisms potential vectors for gene therapy are selected from the viruses which are known to infect these host or can be modified to infect these hosts. In addition to these viral vectors which offer significant efficiencies, native DNA or RNA (not in the context of a viral genome) are also useful for gene therapy. In the case of DNA the cloned gene for the pre-selected protein containing the small molecule-binding site is placed in the DNA sequence such that it is under control of suitable transcription control elements. This engineered DNA is then administered to the organism in such a way that DNA is taken up by cells efficiently resulting in the DNA being either transcribed and translated directly or integrated into the genome followed by transcription and translation. Typically DNA and RNA uptake into cells is poor and this is typically stimulated by the use of various chemical and physical methods. Examples of chemical methods are the use of liposomes, calcium phosphate, detergents, ion-exchange compounds such as DEAE dextran, and also methods linked to specific receptors such as the folate receptor via linkage to folate analogues. The physical methods that have proved valuable for getting DNA into a cell are electroporation, heat, physical membrane perturbation such as pricking, and scrapping of cells.

Pharmaceutical Preparations of the Compounds of the Invention

The pharmacologically active compounds of the subject inventions optionally are combined with suitable pharmaceutically acceptable carriers comprising excipients and auxiliaries which facilitate processing of the active compounds. These are administered as tablets, dragees, capsules, and suppositories. The compositions are administered, for example, orally, rectally, vaginally, pulmonary or released through the buccal pouch of the mouth, and are optionally applied in solution form by injection, orally or by topical administration such as transdermal patchs. The compositions may contain from about 0.1 to 99 percent, preferably from about 50 to 90 percent, of the active compound(s), together with the excipient(s).

For delivery of high molecular weight compounds and compounds with poor bioavailability of the subject invention methods based on various known formulations and methods are contemplated; these include the use of antibodies, pyridoxyl, insulin, transferrin, galactose, sialyl-LewisX, liposomes, asialolglycoprotein, folate, invasin, iontophoresis, galparan, transportan, homeobox peptides (such as those based on antennapedia residues 43–58), for intracellular delivery.

For parenteral administration by injection or intravenous infusion, the active compounds are suspended or dissolved in aqueous medium such as sterile water or saline solution. Injectable solutions or suspensions optionally contain a surfactant agent such as polyoxyethylenesorbitan esters, sorbitan esters, polyoxyethylene ethers, or solubilizing agents like propylene glycol or ethanol. The solution typically contains 0.01 to 5% of the active compounds. The active compounds optionally are dissolved in pharmaceutical grade oils (ie vegetable, synthetic) for intramuscular, sub-cutaneous or sub-dermal injection. Such preparations contain about 1% to 50% of the active compound(s) in oil. Also the active compounds optionally are incorporated into or onto particulate preparations of polymeric compounds such as polylactic acid, polyglycolic acid, hydrogels, etc. or into liposomes, niosomes, microemulsions, micelles, unilamellar or multilamellar vesicles, biodegradable injectable microcapsules or microspheres, or protein matrices, erythrocyte ghosts, spheroplasts, skin patches, or other known methods of releasing or packaging pharmaceuticals.

Suitable excipients include fillers such as sugars, for example lactose, sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch or potato starch, gelatin, tragacanth, methyl cellulose, hydroxypropylmethyl cellulose, sodium carboxymethyl cellulose and/or polyvinyl pyrrolidone.

Auxiliaries include flow-regulating agents and lubricants, for example, silica, talc, stearic acid or salts thereof, such as magnesium stearate or calcium stearate and/or polyethylene glycol. Dragee cores are provided with suitable coatings which, if desired, are resistant to gastric juices. For this purpose, concentrated sugar solutions are used, which optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate are used. Dyestuffs or pigments are optionally added to the tablets or dragee coatings, for example, for identification or in order to characterize different compound doses.

The pharmaceutical preparations of the present invention are manufactured in a manner which is itself known, for example, by means of conventional mixing, granulating, dragee-making, dissolving, or lyophilizing processes. Thus, pharmaceutical preparations for oral use are obtained by combining the active compound(s) with solid excipients, optionally grinding the resulting mixture and processing the mixture of granules, after adding suitable auxiliaries, if desired or necessary, to obtain tablets or dragee cores.

Other pharmaceutical preparations which are useful for oral delivery include push-fit capsules made of gelatin, as well as soft-sealed capsules made of gelatin and a plasticizer such as glycerol or sorbitol. The push-fit capsules contain the active compound(s) in the form of granules which optionally are mixed with fillers such as lactose, binders such as starches and/or lubricants such as talc or magnesium stearate, and, optionally stabilizers. In soft capsules, the active compounds are preferably dissolved or suspended in suitable liquids such as fatty oils, liquid paraffin, or polyethylene glycols. In addition, stabilizers optionally are added.

Suitable formulations for parenteral administration include aqueous solutions of the active compounds in water soluble form, for example, water soluble salts. In addition, suspensions of the active compounds as appropriate in oily injection suspensions are administered. Suitable lipophilic solvents or vehicles include fatty oils, for example, sesame oil, or synthetic fatty acid esters, for example, ethyl oleate or tri-glycerides. Aqueous injection suspensions optionally include substances which increase the viscosity of the suspension which include, for example, sodium carboxymethylcellulose, sorbitol and/or dextran. The suspension optionally contains stabilizers.

In another embodiment, the active compounds are formulated as part of a skin lotion for topical administration. Suitable lipophilic solvents or vehicles include fatty oils, for example sesame oil or coconut oil, or synthetic fatty acid esters, for example ethyl oleate or triglycerides.

In another embodiment, the active compounds are formulated in vehicles suitable for direct treatment of gastrointestinal mucosa. Examples include mouthwashes, liquids (solutions or suspensions) to be swallowed, or viscous fluids (e.g. solutions of methylcellulose, carboxymethylcellulose, xanthan gum, etc.) which are administered orally or rectally.

Other pharmaceutical preparations which are used rectally, especially for treatment of the colon and rectum, include, for example, suppositories which consist of a combination of active compounds with a suppository base. Suitable suppository bases are, for example, natural or synthetic triglycerides, paraffin hydrocarbons, polyethylene glycols or higher alkanols. In addition, gelatin rectal capsules which consist of a combination of the active compounds with a base are useful. Base materials include, for example, liquid triglycerides, polyethylene glycols, or paraffin hydrocarbons.

Other pharmaceutical preparations which are used orally, especially for treatment of the lungs, trachea, sinus and oral cavity, include, for example, powders, foamates, nanoparticles, liposomes, niosomes, microemulsions, micelles, unilamellar or multilamellar vesicles. These may optionally be administered as for example sprays and aerosols.

The following examples are illustrative, but not limiting of the compositions and methods of the present invention. Other suitable modifications and adaptations of a variety of conditions and parameters normally encountered which are obvious to those skilled in the art are within the spirit and scope of this invention.

EXAMPLES

Example 1

Targeted Degradation of HIV Integrase
Expression and Purification of $His_6$-HIV Integrase Full length HIV-1 IN is expressed in *E. coli* and purified by the established protocols of Craigie, R., Hickman, A. B. and Engelman, A. (1995) in HIV Volume 2: A Practical Approach, pp53–71, J. Karn ed., Oxford Univ. Press, New York. The pINSD.His plasmid, containing the HIV-1$_{NL4-3}$ coding sequence inserted in the pET-15b $His_6$ expression vector (Novagen), is available from the NIAID AIDS Research and Reference Reagent Program as transformed HB101. pINSD.His is prepared using a Qiagen plasmid purification kit, and transformed into BL21(DE3) by electroporation for expression in shaker flask cultures by Protocol 2, from Craigie, R., Hickman, A. B. and Engelman, A. (1995) in HIV Volume 2: A Practical Approach, pp53–71, J. Karn ed., Oxford Univ. Press, New York. Following Protocol 4, as described in Craigie, R., Hickman, A. B. and Engelman, A. (1995) in HIV Volume 2: A Practical Approach, pp53–71, J. Karn ed., Oxford Univ. Press, New York, bacteria are lysed and the $His_6$ HIV IN purified under native conditions. The protocol is basically a one step chelating column purification of a 2 M NaCl-soluble lysate fraction.

Synthesis of Bifunctional Trans-Targeting Derivatives of L-Chicoric Acid

Compounds are designed based on bromoacetic acid derivatization, via ethylenediamine, of an L-chicoric acid carboxyl group for selective reaction with thiols. Linkers are composed of aminocaproic acid and β-alanine, variations of this are readily synthesized by solid phase methods to include cysteine for conjugation to bromo acetylated L-chicoric acid. Thiol addition to bromoacetic acid is selective, accomplished under mild reaction conditions, and yields are near quantitative (Inman, J. K., Highet, P. F., Kolodny, N., and Robey, F. A. (1991) Bioconjugate Chem. 2, 458–463). A significant aspect of this strategy is that once L-chicoric acid has been successfully bromoacetylated and purified, any number of different trans-targeting compounds are obtained easily and in high yield from recognition/linker "cassettes" generated readily from solid phase synthesis.

Figure 2:
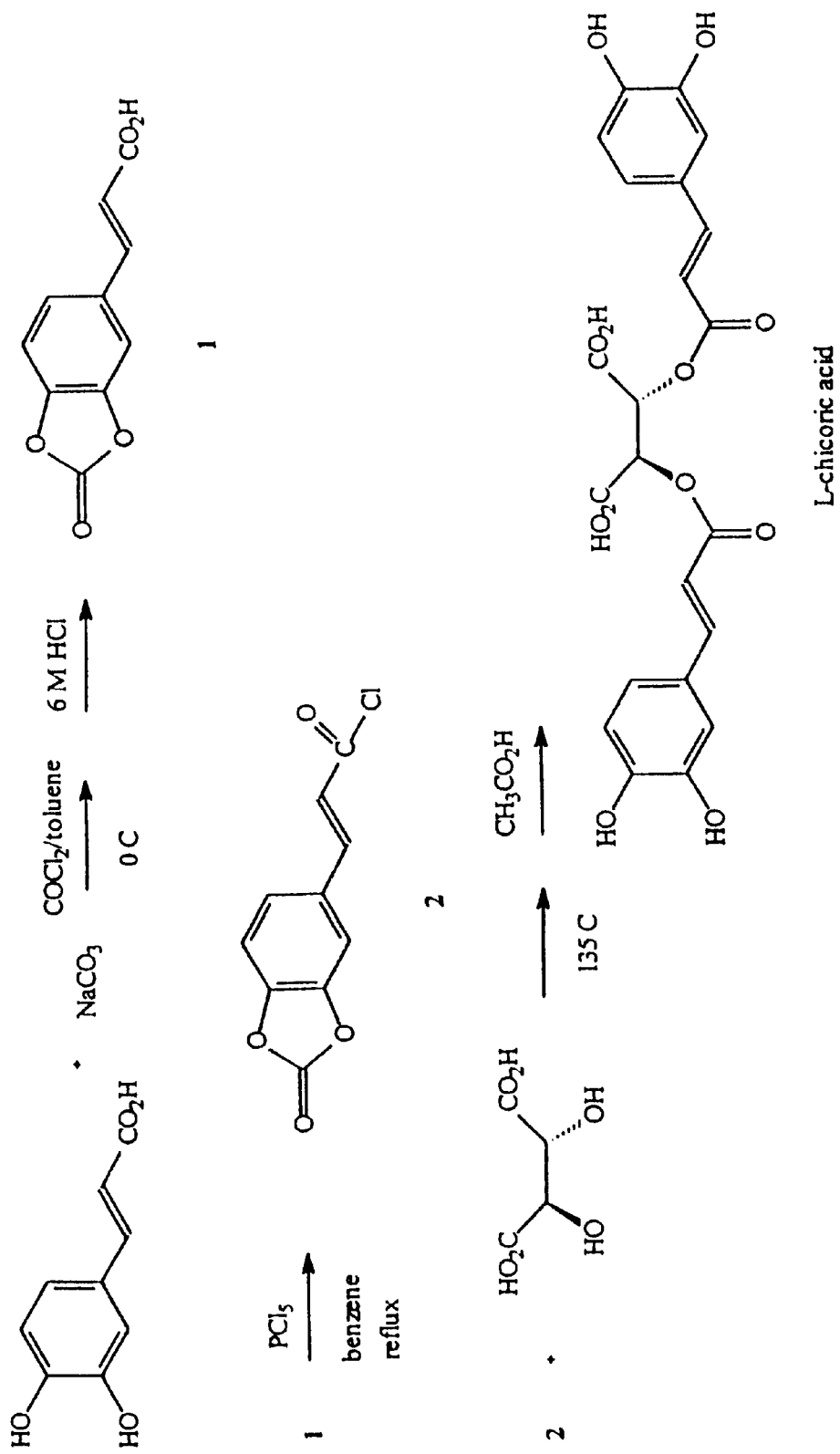
FIG. 2 shows the synthetic steps for synthesis of L-chicoric acid.

The synthesis of L-chicoric acid is accomplished following literature procedures (Panizzi, L., Scarpati, M. L. and Scarpati, R. (1954) Gazz. Chim. Ital. 84, 806–815, Scarpati, M. L. and Oriente, G. (1958) *Tetrahedron* 4, 43–48, FIG. 2). The bromoacetyl derivatization strategy is to generate bromoacetic acid anhydride for reaction with commercially available Boc-blocked ethylenediamine (Aldrich) to give N-bromoacetyl-ethylenediamine after TFA deprotection and crystallization (4, FIG. 3, Scheme 2). 4 is conjugated to L-chicoric acid activated with NHS at one of the symmetrically equivalent carboxylate groups. NHS ester activation of acid groups for primary amine coupling is used routinely in conjugation chemistry. Preparative RP HPLC is used for purification of the desired monoester product from the reaction mixture. The conjugation reaction to give the final bromoacetyl derivative of L-chicoric acid, 6, is straightforward in terms of mixture complexity and product purification. NMR and mass spectral analysis monitor all steps of the synthesis.

The E3α ubiquitination recognition elements are based on the studies by Bachmair, A. and Varshavsky, A. (1989) Cell 56, 1019–1032. The aminocaproic acid (εAhx) and β-Ala will give the ubiquitination recognition elements considerably more degrees of freedom than a peptide and are not susceptible to proteinases. Combinations of aminocaproic acid and β-Ala are used to adjust hydrophobic character, flexibility and particularly the length of the linkers. Changing between Type I (basic) and Type II (hydrophobic) recognition signals significantly affect the hydrophobic character of the trans-targeting compounds, but have an effect on linker function since these sites are spatially distinct on E3α.

The first series of recognition/linkers include Arg (Type I) and Phe (Type II) recognition components and three different spacer elements; εAhx-Cys, β-Ala-εAhx-Cys, and εAhx-εAhx-Cys with molecular weights of approximately 315, 386 and 428, respectively.

Solid Phase Synthesis of E3α Recognition/linker Components (Ubiquitination Recognition Elements)

Various ubiquitination recognition elements were synthesized by solid phase peptide synthesis and characterized by $C_{18}$ reverse phase HPLC and MALDI-TOF mass spectral analysis (American Peptide Company, Inc., Sunnyvale, Calif.). The linker elements include caproic acid (εAhx) and beta-alanine (β-Ala) for a high degree of freedom of motion, and a C-terminal Cys residue for specific thiol conjugation to targeting molecule components. The compounds were synthesized to >90% purity in 10 mg amounts.

|  | MW |
| --- | --- |
| Arg-εAhx-Cys | 390 |
| Arg-β-Ala-εAhx-Cys | 462 |
| Arg-εAhx-εAhx-Cys | 521 |
| Phe-εAhx-Cys | 400 |
| Phe-β-Ala-εAhx-Cys | 452 |
| Phe-εAhx-εAhx-Cys | 531 |

Further ubiquitination recognition elements are synthesized as follows using methods described above.
1. Arg-Ala-εAhx-Cys
2. Arg-Ala-β-Ala-εAhx-Cys (SEQ ID NO:66)
3. Arg-Ala-εAhx-εAhx-Cys
4. Phe-Ala-εAhx-Cys
5. Phe-Ala-β-Ala-εAhx-Cys (SEQ ID NO:67)
6. Phe-Ala-εAhx-εAhx-Cys Synthesis of L-chicoric Acid FIG. 2, Scheme 1.

To 0.36 g of caffeic acid (Aldrich) in 100 mL of $H_2O$ is added 10 g of sodium bicarbonate and the solution is cooled to 0° C. A 20% solution of $COCl_2$ in toluene (Fluka) is added slowly with stirring, followed by the slow addition of 20 mL of 6 M HCl. The solid product is filtered under vacuum, washed with $H_2O$ and acetone, and recrystallized from glacial acetic acid to give the blocked catechol of caffeic acid, 3 (Panizzi, L., Scarpati, M. L. and Scarpati, R. (1954) Gazz. Chim. Ital. 84, 806–815).

To 0.25 g of 3 in benzene is added 0.30 g of $PCl_5$ and the reaction mixture is refluxed until 20 min after complete solution, and then allowed to stand for 1 hr. The solid product is rapidly filtered under vacuum, washed with ether, and dried under vacuum to yield 4 (Panizzi, L., Scarpati, M. L. and Scarpati, R. (1954) Gazz. Chim. Ital. 84, 806–815).

A mixture of 0.23 g of 4 and 86 mg of L-tartaric acid (Aldrich) is heated on an oil bath under reduced pressure until fusion at 115° C. The reaction temperature is increased to 135° C. for 10 min, and the reaction is allowed to cool. The solid product is heated with 4.5 mL of 80% acetic acid on a steam bath until dissolved, and then rotovapped. The residue is heated at 50° C. with 1.25 mL of $H_2O$, and the mixture filtered to remove unreacted caffeic acid. The filtrate is extracted 2× with ether, and the ether layer is rotovapped. The residue is taken up into $H_2O$ with warming and adjusted to pH 6 with sodium bicarbonate. Caffeic acid is precipitated as a barium salt by the addition of saturated $BaSO_4$, collected and washed with 3% $BaSO_4$ by microcentrifugation, and then mixed with 0.75 mL 2 M HCl and 2 mL ether until in solution. The ether layer is removed and the aqueous phase extracted 2× with ether. The combined ether extracts are dried over $MgSO_4$, rotovapped, and the product recrystallized from $H_2O$ to yield L-chicoric acid (Scarpatti and Oriente, 1958).

Figure 3:
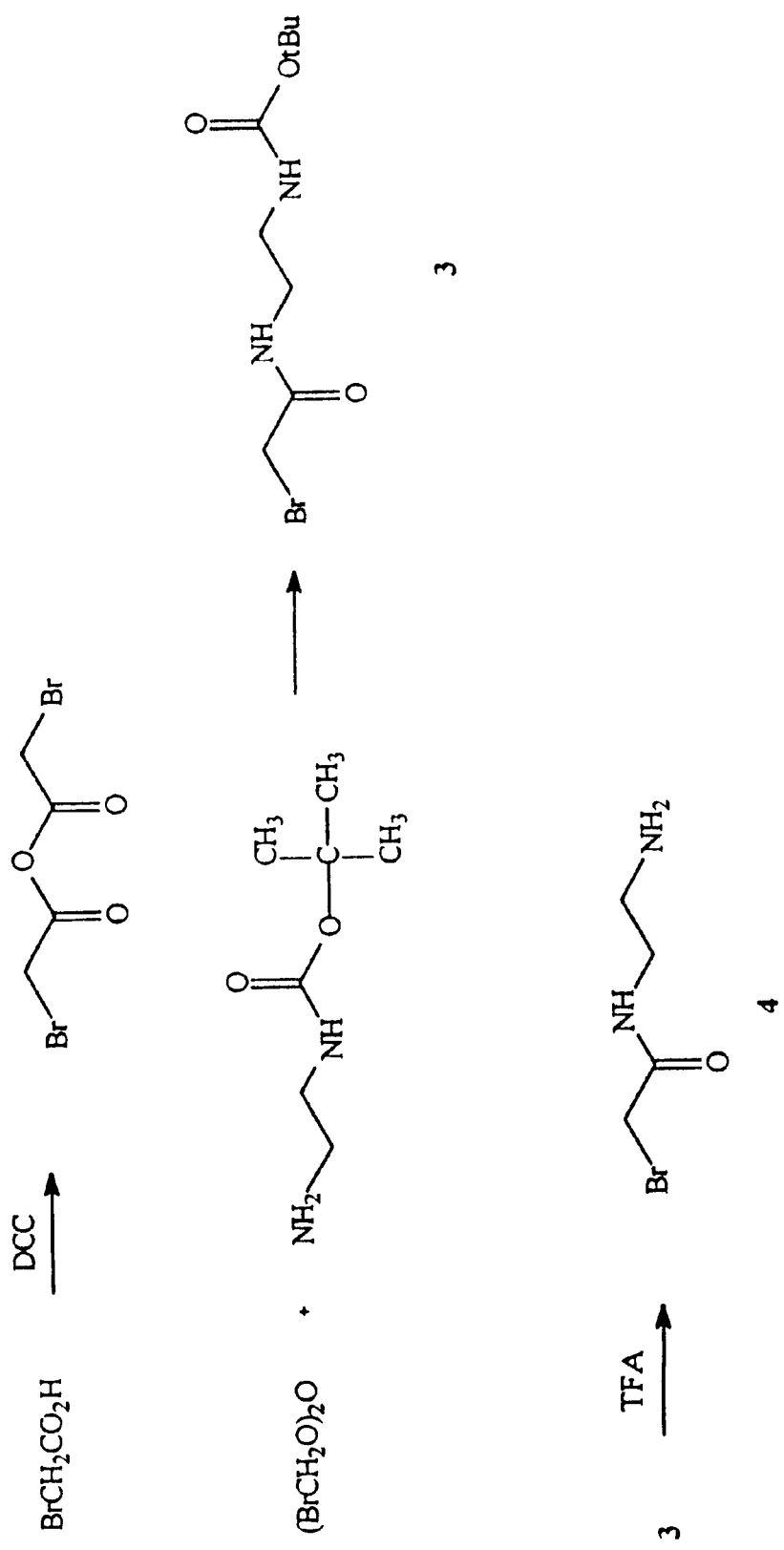
FIG. 3 shows the synthetic steps for synthesis of N-bromoacetyl ethylenediamine

Symmetric Anhydride of Bromoacetic (chloroacetic) Acid
FIG. 3, Scheme 2.

A pre-cooled 0.5 M solution of DCC in DCM (40 ml, 20 mmol) is added to a stirred solution of bromoacetic acid (40 mmol) in DCM (20 ml) at 0° C. The reaction mixture is stirred for 30 min and filtered to remove the dicyclohexylurea that have formed, and the filtrate is evaporated on a rotary evaporator at 20° C. (Bioconjugate Chemistry 1995, 6, 269).

N-bromoacetyl-N'-Boc-ethylenediamine (3)
FIG. 3, Scheme 2.

Freshly prepared bromoacetic anhydride (20 mmol) is dissolved in 10 ml of acetonitrile, and the solution is added to a stirred solution of N-Boc-ethylenediamine (18 mmol, Aldrich) and TEA (20 mmol) in THF (20 ml) at 20° C. The progress of the reaction if followed by the ninhydrin test for free amines. When all Boc-ethylenediamine is consumed the reaction mixture is concentrated on a rotovap and dissolved in ethyl acetate (150 ml). The solution is successively washed with 0.5 M sodium bicarbonate (50 ml×2), 0.1 M sulfuric acid (50 ml×3), brine (50 ml×2), dried over sodium sulfate and concentrated providing the desired N-bromoacetyl-N'-Boc-ethylenediamine (3).

N-bromoacetyl-ethylenediamine (4)
FIG. 3, Scheme 2.

N-bromoacetyl-N'-BOC-ethylenediamine (3) is dissolved in 50% TFA in dichloromethane (5 ml of the solution per mmol of 3) at 20° C. The deprotection is allowed to proceed for 30 min, then the reaction mixture is concentrated on a rotary evaporator and solidifies upon addition of dry ethyl ether. The solid material is filtered off, washed with ether/petroleum ether on filter and dried. The desired N-bromoacetyl-ethylenediamine is obtained in the form of triflouroacetate salt.

Figure 4:
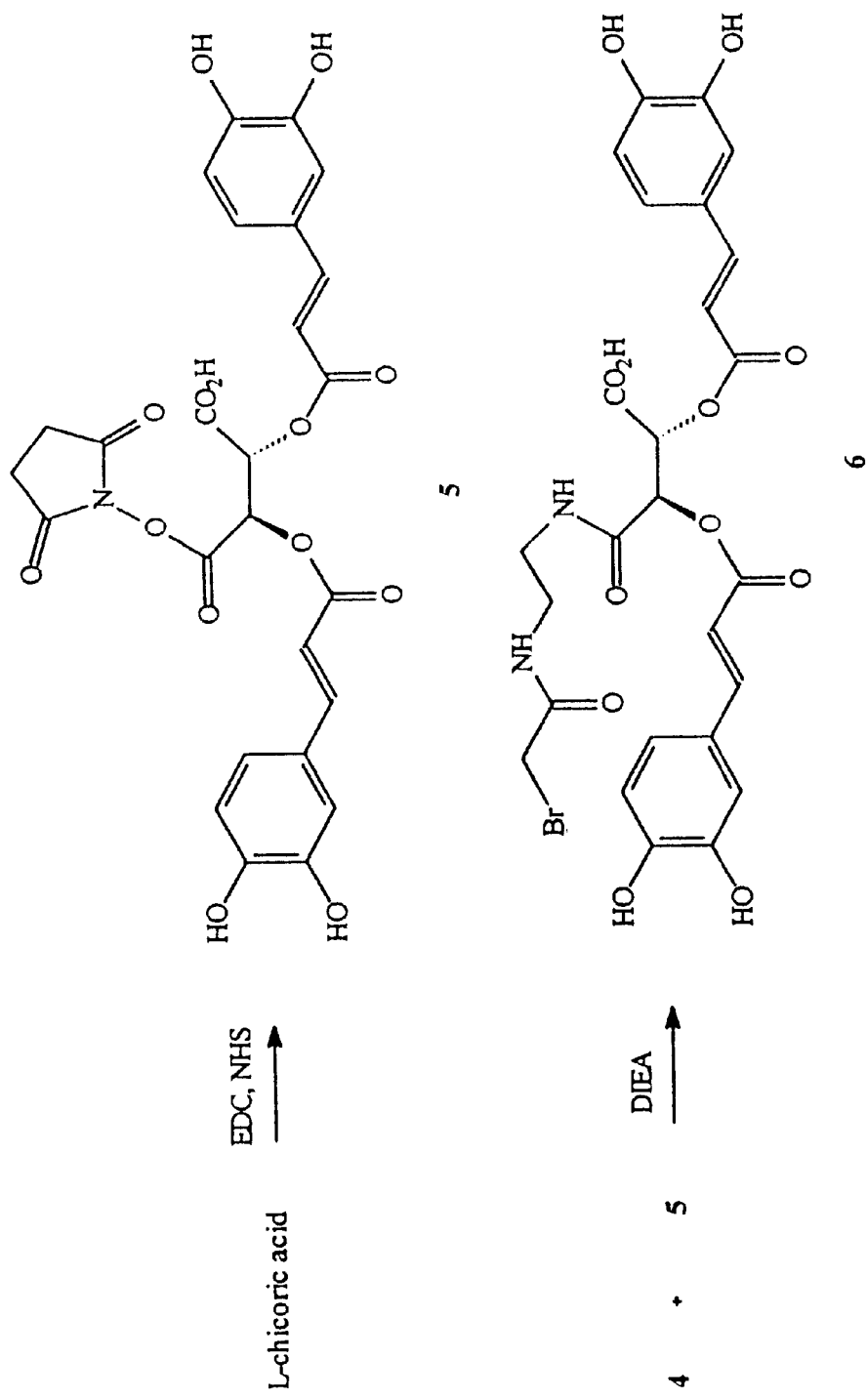
FIG. 4 shows the synthetic steps for synthesis of bromoacetylated L-chicoric acid.

Bromoacetylated Derivative of L-chicoric Acid (6)
FIG. 4, Scheme 3.

Mono NHS ester of L-chicoric acid (5, 0.1 mmol) is added to an excess of the N-bromoacetyl-ethylenediamine (0.2 mmol) in a small volume of THF in presence of DIEA (0.1 mmol). When all the activated ester is consumed, the reaction mixture is diluted with ethyl acetate (150 ml), successively washed with 0.1 M sulfuric acid (100 ml×2) to remove the unreacted amine, brine (50 ml×2), dried over sodium sulfate and evaporated on a rotovap. 6 is further purified by crystallization from appropriate solvents or by preparative RP HPLC.

Figure 5:
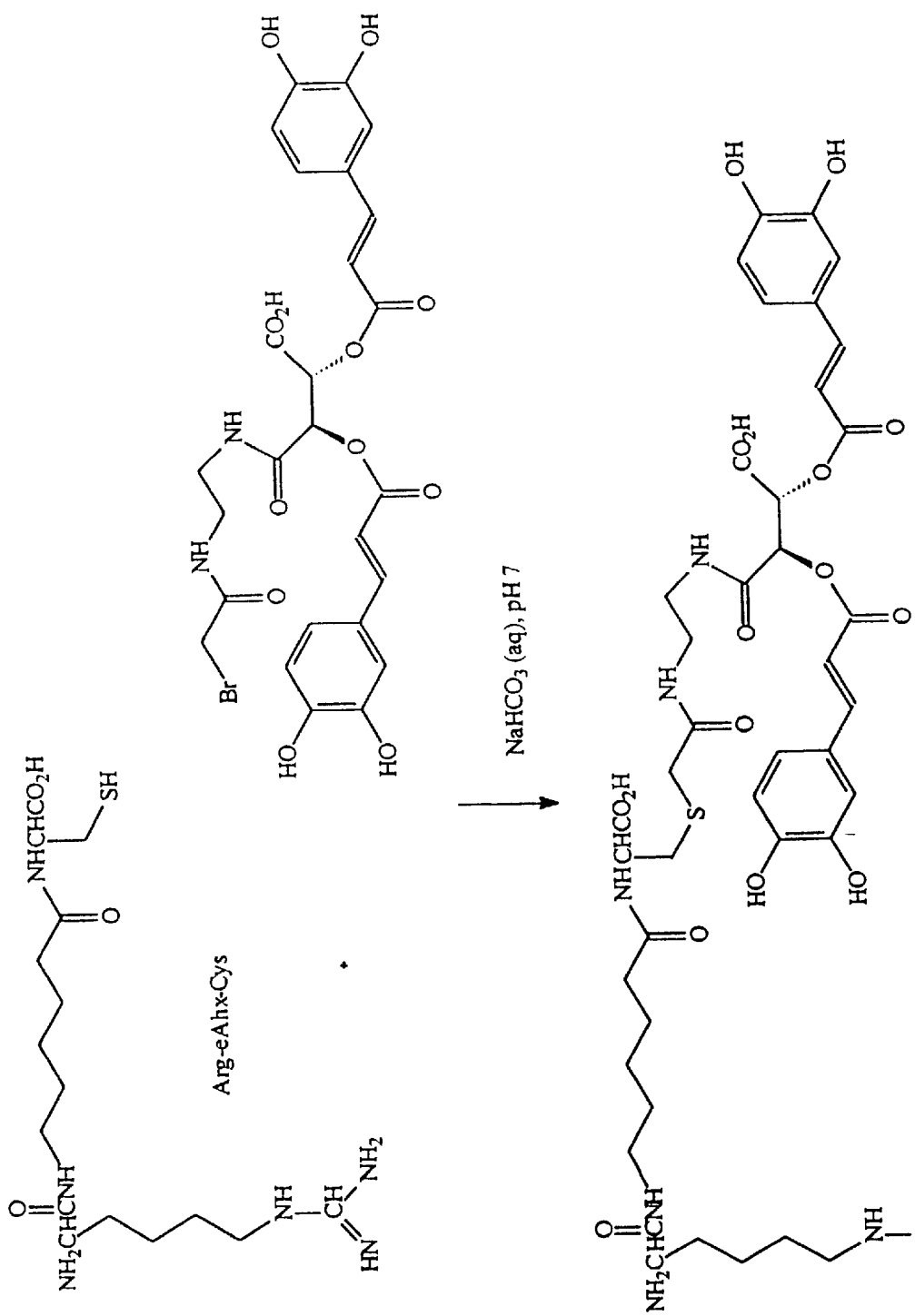
FIG. 5 shows the conjugation of the ubiquitination recognition element to L-chicoric acid.

Conjugation of 6 with the Recognition/linkers;
FIG. 5, Scheme 4.

The recognition/linkers from solid phase synthesis (50 μmol) and 6 (60 μmol) are dissolved in a small volume of 50 mM sodium acetate buffer, pH 4.0 and purged with nitrogen. pH of the solution is raised up to 7–8 by addition of solid sodium bicarbonate. The reaction mixture is stirred at 20° C. until the Elman test shows absence of free thiols in the mixture. The reaction mixture is diluted with 0.1% trifluoroacetic acid and the desired product is isolated by preparative RP HPLC (Ivanov, B., Grzesik, W., and Robey, F. A. (1995) Bioconjugate Chem. 6, 269–277).

In Vitro Reticulocyte Extract Assay for Targeted Degradation

Degradation is monitored using $^{125}$I-labeled IN in a rabbit reticulocyte lysates by SDS-PAGE/auto radiography and by determination of soluble $^{125}$I after the precipitation of proteins with TCA. The use of this system to assess ubiquitin-dependent proteolysis is straightforward and well established in the literature (Gonda, D. K., Bachmair, A., Wunning, I., Tobias, J. W., Lane, W. S. and Varshavsky, A. (1989) J. Biol. Chem. 264, 16700–16712, Hershko, A., Ciechanover, A., Heller, H., Haas, A. L., and Rose, I. A. (1980) Proc. Natl. Acad. Sci. USA 77, 1783–1786).

The series of trans-targeting compounds are evaluated for their ability to initiate the degradation of [$^{125}$I]-IN in the reticulocyte lysates. SDS-PAGE time course results show transitory multiubiquitinated IN species, followed by loss of $^{125}$I-labeled protein. The assay for TCA-soluble peptide product fragments is used to better quantitate rates of degradation and effective concentrations.

Preparation of Rabbit Reticulocyte Lysates

Biocon, Inc. (Rockville, Md.) performed the induction and collection of reticulocytes from NZW rabbits. A female NZW rabbit weighing less than 2 kg was injected subcutaneous with 0.6 mL/kg of 20 mg/mL phenylhydrazine on day 1,2,4 and 6. On day 8 the rabbit was anesthetized with ketamine and bled out by heart bleed. The blood was collected into heparinized tubes on ice, and washed 3 times with 5 pellet volumes per wash of cold PBS. The reticulocyte lysates were prepared by the addition of 1.5 volumes of cold $H_2O$ 1 mM DTT per volume of packed cells, followed by centrifugation for 2.5 hrs at 38,400×g. The supernatant was frozen in aliquots at −80° C. The reticulocyte lysate can be used for 2 or 3 freeze/thaw cycles only.

TCA Precipitation Assay of [$^{125}$I]-protein Degradation in Reticulocyte Lysates Proteins were labeled by Lofstrand Laboratories Ltd. (Gaithersburg, Md.) Labeled to 0.12–0.50 μCi/μg by oxidation of Na$^{125}$I using an iodobead chloramine-T procedure.

The ubiquitin-dependent protein degradation assay was preformed by the addition of 70 μL of rabbit reticulocyte lysate and 5 μL of 0.06 μCi/μL $^{125}$I-labeled protein to 175 mL of reaction buffer containing 40 mM Tris pH 7.6, 2 mM DTT, 5 mM MgCl$_2$, 0.5 mM ATP, 35 μg creatine phosphokinase (Sigma) and 10 mM phosphocreatine. The reaction were run at 37 C in a heating block, and at time points 30 μL of the reaction was transferred to 50 μL of cold 100 mg/mL BSA and protein was precipitated by the addition of 420 μL of 23% TCA followed by 15 min on ice. The precipitated samples were microfuged for 2 min at 5000 rpm and 300 μL of supernatant was then counted for TCA-soluble $^{125}$I on a gamma counter (Hidex).

Results for [$^{125}$I]-lysozyme(hen, Sigma), [$^{125}$I]-glutathione S-transferase Degradation The N-terminal sequences for lysozyme and GST samples submitted to Midwest Analytical were KVFGR and PPYTI, respectively. The only N-end rule stabilizing residues in mammalian cells are Gly, Val, Pro, and Met. Lysozyme is the usual positive control for the reticulocyte lysate assays; GST should be stable to N-end rule, ubiquitin-dependent proteolysis. Time points were taken every 30 min from 0 to 120 min. 25 μL rxn samples counted directly in the gamma counter gave 55746 cpm for lysozyme and 45989 cpm for GST. Results demonstrated that the assay was functional for the specific N-end rule degradation as described in the literature.

| Time | Lysozyme | GST |
|---|---|---|
| 0 | 1338 | 1320 |
| 30 | 7512 | 1474 |
| 60 | 11979 | 1723 |
| 90 | 14976 | 1863 |
| 120 | 16337 | 2173 |

Table 1, Time course of lysozyme and glutathione S-transferase ubiquitin mediated degradation in the reticulocyte lysate SDS-PAGE $^{125}$I Protein Degradation Assay The ubiquitin-dependent protein degradation assay was preformed by the addition of 70 μL of rabbit reticulocyte (or other cell) lysate and 5 μL of 0.06 μCi/μL $^{125}$I-labeled protein to 175 mL of reaction buffer containing 40 mM Tris pH 7.6, 2 mM DTT, 5 mM MgCl$_2$, 0.5 mM ATP, 35 μg creatine phosphokinase (Sigma) and 10 mM phosphocreatine. The reaction was run at 37 C in a heating block, and at time points 30 μL of the reaction are transferred to gel loading buffer. Samples are run on tricine 10–20% SDS-PAGE gels (Novex) for autoradiography on X-omat film (Kodak) to determine $^{125}$I protein degradation.

Example 2

Selection, Discovery and/or Evaluation of Ubiquitination Recognition Elements

In order to determine if a given molecule or molecular element is potentially valuable as a ubiquitination recognition element the assay described above is run with [$^{125}$I]-lysozyme or other labeled protein substrates in the presence of potential ubiquitination recognition elements.

In the case of Arg-εAhx-Cys, Phe-εAhx-Cys these were run in the reticulocyte lysate using lysozyme and both demonstrated inhibition of the lysozyme degradation as expected for ubiquitination recognition elements. The results at the 2 hour time point were 12,475 cpm for no treatment, 6,486 cpm for the 2 mM Arg-εAhx-Cys treatment and 3,592 cpm for the 5 mM Phe-εAhx-Cys treatment. These results indicate that a ubiquitination recognition element can be made from X-εAhx-linker where X is an amino acid involved in the N-end recognition and the linker is chemistry which links this to a binding molecule for the target protein of interest.

In an additional assay for ubiquitination recognition elements compounds and peptides are added to HeLa or Jurkat cell extracts (Alkalay et al 1995, Proc. Natl. Acad. USA 92, 10599), containing radiolabeled IkappaB alpha or IkappaB beta, modulation of the ubiquitination was monitored by gel electrophoresis of the labeled proteins. This allows the selection of ubiquitination recognition elements specific for the ubiquitination pathway used for IkappaB degradation (Yaron A, 1997, EMBO J. 16, 6486).

Example 3

Targeted Degradation of Glutathione S-transferase

Figure 6:
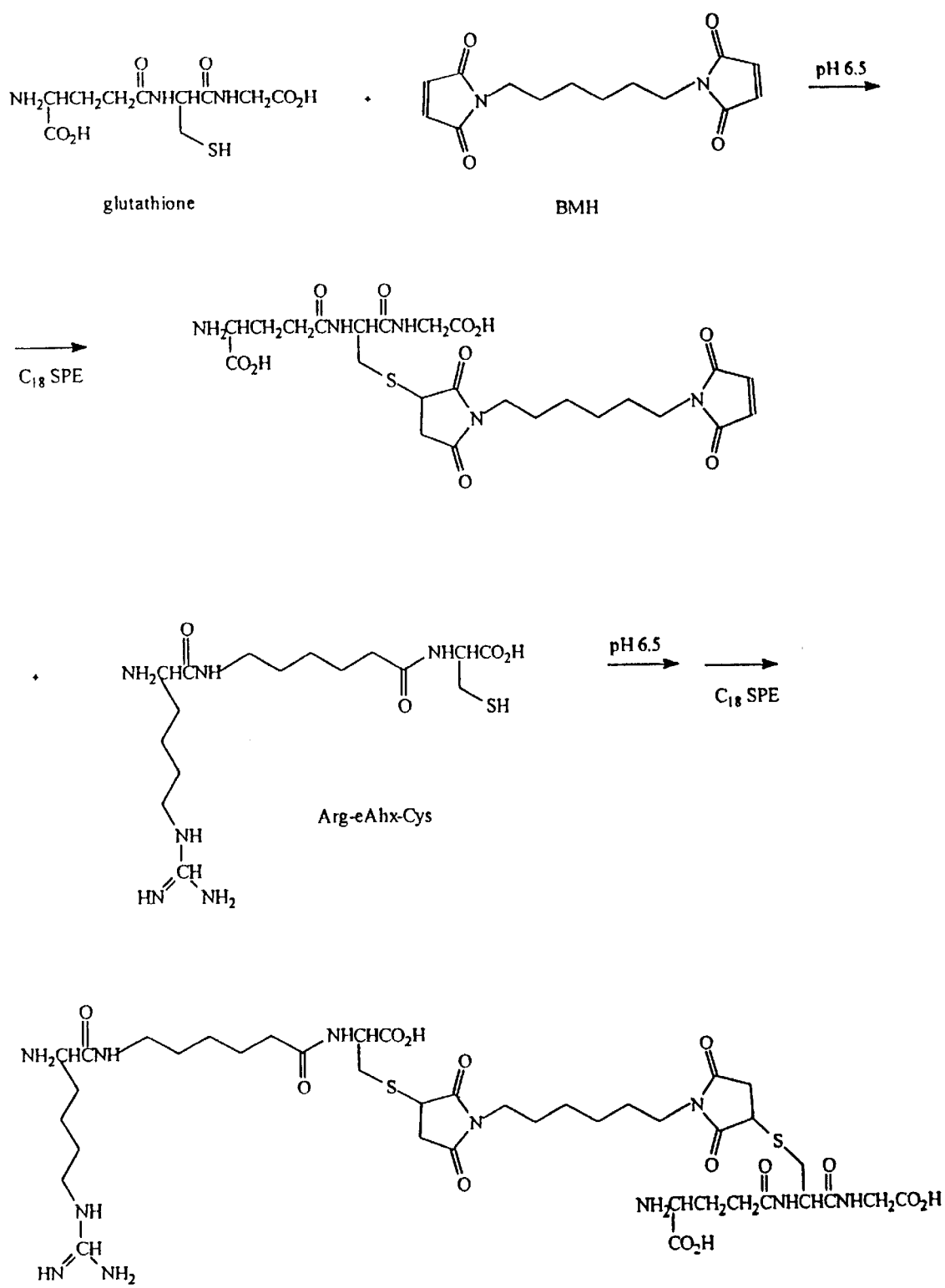
FIG. 6 shows the synthetic steps for synthesis of ubiquitination recognition element linked to glutathione.

Conjugation of Ubiquitination Recognition Elements to Glutathione (FIG. 6)

4.18 mg (15.1 μmol) bismaleimidohexane (BMH, Pierce, Rockford, Ill.) in 200 μL of dimethylformamide was added slowly to 1.84 mg (6 μmol) glutathione in 2 mL 20 mM potassium phosphate pH 7.0 The reaction was followed by $C_{18}$ reverse phase HPLC. After 30 min at room temperature, the reaction mixture was centrifuged at 12,000 rpm for 2 min to remove precipitate, and the sample was loaded onto a $C_{18}$ Sep-Pak cartridge pre-equilibrated with $H_2O$. The bound sample was washed with 2 mL of 10% methanol/$H_2O$ and eluted in 3 1-mL fractions of 50% methanol. The second 1 mL product fraction was partially concentrated by evaporation of the methanol. This activated glutathione was then reacted with the various ubiquitination recognition elements.

For example for Arg-εAhx-Cys the activated glutathione was added to 50 μL of 20 mg/mL Arg-εAhx-Cys. The pH was adjusted to pH 6.5 by the addition of 5 M sodium hydroxide and the reaction was followed by $C_{18}$, reverse phase HPLC. This protocol repeated for the following ubiquitination recognition elements, Arg-εAhx-Cys, Arg-β-Ala-εAhx-Cys, Arg-εAhx-εAhx-Cys, Phe-εAhx-Cys, Phe-β-Ala-εAhx-Cys, Phe-εAhx-εAhx-Cys, KKERLLD-DRHDSGLDSMKDEEC (SEQ ID NO 50) where the S in bold are phosphorylated, RAALAVLKSGNC (SEQ ID NO 51), HGFPPEVEEQDVGTLPISCAQESGMDRHC (SEQ ID NO 52). This generated a series of compounds for testing in the rabbit reticulocyte, HeLa cell and Jurkat cell lysates.

Glutathione S-transferase (Sigma, St. Louis, Mo.) was labeled by Lofstrand Laboratories Ltd. (Gaithersburg, Md.) Labeled to 0.12–0.50 μCi/μg by oxidation of $Na^{125}I$ using an iodobead chloramine-T procedure.

The ubiquitin-dependent protein degradation assay was preformed by the addition of 70 μL of rabbit reticulocyte (or other cell) lysate and 5 μL of 0.06 μCi/μL $^{125}$I-labeled Glutathione S-transferase to 175 mL of reaction buffer containing 40 mM Tris pH 7.6, 2 mM DTT, 5 mM $MgCl_2$, 0.5 mM ATP, 35 μg creatine phosphokinase (Sigma) and 10 mM phosphocreatine. To demonstrate the targeted degradation of the GST, various concentrations of the compounds from the above synthesis were added to the lysate (10 to 0.001 mM). The reaction were run at 37 C in a heating block, and at time points 30 μL of the reaction was transferred to 50 μL of cold 100 mg/mL BSA and protein was precipitated by the addition of 420 μL of 23% TCA followed by 15 min on ice. The precipitated samples were microfuged for 2 min at 5000 rpm and 300 μL of supernatant was then counted for TCA-soluble $^{125}$I on a gamma counter (Hidex). Time points are taken every 30 min from 0 to 120 min. Results demonstrate targeted degradation.

Example 4

Targeted Degradation of Anti Fluorescein Antibody

Figure 7:
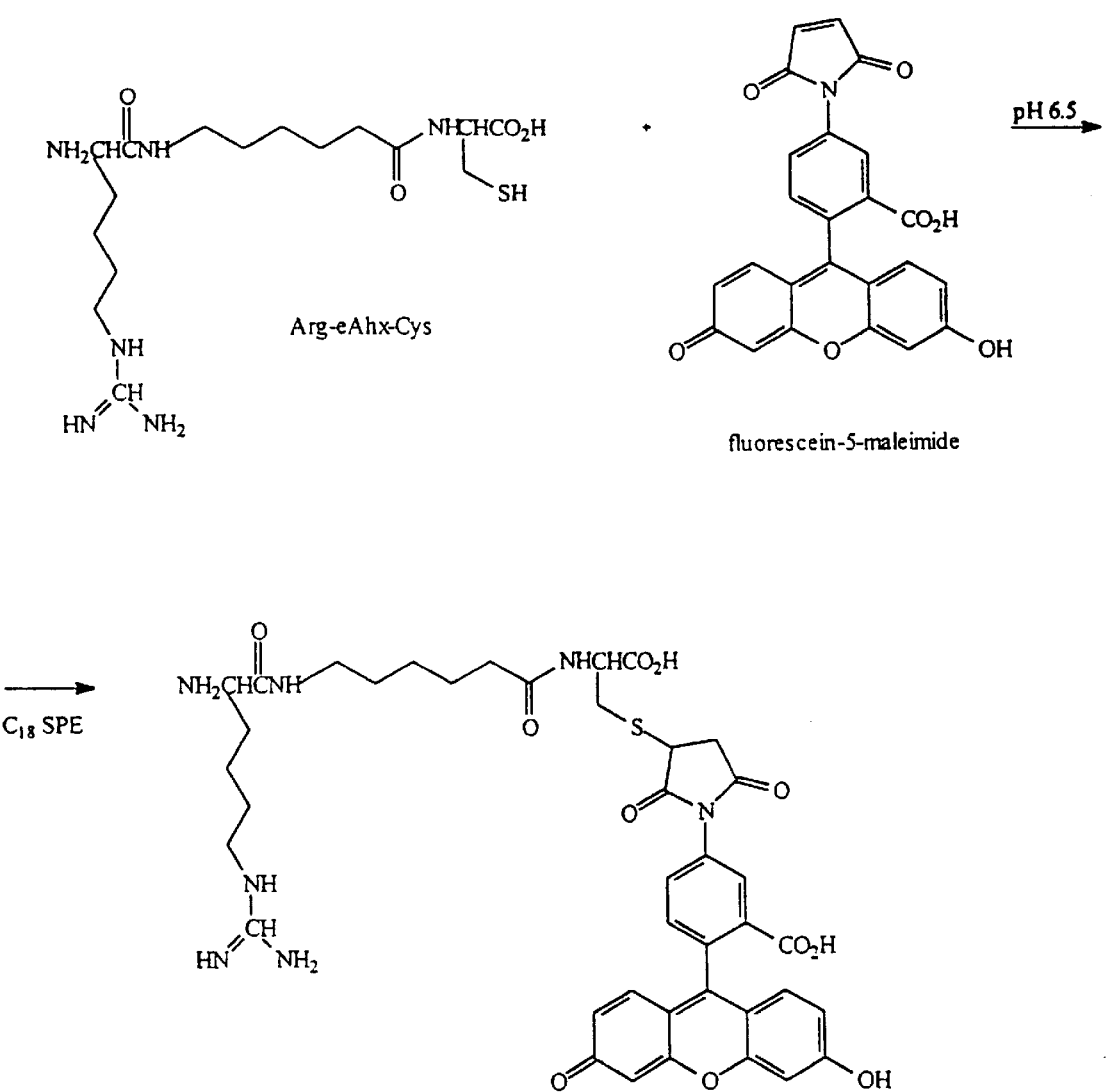
FIG. 7 shows the synthetic steps for synthesis of ubiquitination recognition element linked to fluorescein.

Conjugation of Ubiquitination Recognition Elements to Fluorescein-5-maleimide (FIG. 7)

Arg-εAhx-Cys. To 400 μL of 5 mg/mL Arg-εAhx-Cys (2.00 mg, 5.13 μmol) was added 219 μL of 50 mg/mL fluorescein-5-maleimide in dimethylformamide (Pierce, 10.95 mg, 25.65 μmol, 5-fold molar excess) and the pH was adjusted to pH 6.5 with 5 M sodium hydroxide. The reaction was followed by $C_{18}$ reverse phase HPLC. After 60 min at room temperature, the sample was loaded onto a $C_{18}$ Sep-Pak cartridge pre-equilibrated with $H_2O$. The bound sample was washed with 2 mL of 10% methanol/$H_2O$ and the product eluted in 31 mL fractions of 60% methanol. This protocol is repeated for the following ubiquitination recognition elements, Arg-εAhx-Cys, Arg-β-Ala-εAhx-Cys, Arg-εAhx-εAhx-Cys, Phe-εAhx-Cys, Phe-β-Ala-εAhx-Cys, Phe-εAhx-εAhx-Cys, KKERLLDDRHDSGLDSMKDEEC (SEQ ID NO 50) where the S in bold are phosphorylated, RAALAVLKSGNC (SEQ ID NO 51), HGFPPEVEEQDVGTLPISCAQESGMDRHC (SEQ ID NO 52). This generated a series of compounds for testing in the rabbit reticulocyte lysate.

Anti fluorescein antibodies (Fitzgerald and Molecular Probes, Oreg.) was labeled by Lofstrand Laboratories Ltd. (Gaithersburg, Md.) Labeled to 0.12–0.50 μCi/μg by oxidation of $Na^{125}I$ using an iodobead chloramine-T procedure.

The ubiquitin-dependent protein degradation assay was preformed by the addition of 70 μL of rabbit reticulocyte (or other cell) lysate and 5 μL of 0.06 μCi/μL $^{125}$I-labeled anti fluorescein antibody to 175 mL of reaction buffer containing 40 mM Tris pH 7.6, 2 mM DTT, 5 mM $MgCl_2$, 0.5 mM ATP, 35 μg creatine phosphokinase (Sigma) and 10 mM phosphocreatine. To demonstrate the targeted degradation of the anti fluorescein antibodies, various concentrations of the compounds from the above synthesis were added to the lysate (10 to 0.001 mM). The reaction were run at 37 C in a heating block, and at time points 30 μL of the reaction was transferred to 50 μL of cold 100 mg/mL BSA and protein was precipitated by the addition of 420 μL of 23% TCA followed by 15 min on ice. The precipitated samples were microfuged for 2 min at 5000 rpm and 300 μL of supernatant was then counted for TCA-soluble $^{125}$I on a gamma counter (Hidex). Time points are taken every 30 min from 0 to 120 min. Results demonstrate the targeted degradation.

Example 5

Targeted Degradation of Thioredoxin

Conjugation of Ubiquitination Recognition Elements to 4-aminophenyl Arsenoxide.

Arg-εAhx-Cys. To 1.83 mg (10 μmol) 4-aminophenyl arsenoxide in 100 μL dimethylformamide was added 5.3 μL of 50 mg/mL ethylene glycobis(sulfo-succinimidylsuccinate) (Pierce, 15 μmol, 1.5 equivalents) in dimethyformamide. After 30 min reaction time at room temperature, 2.0 mg (5.13 μmol) Arg-εAhx-Lys in 400 μL 20 mM potassium phosphate pH 6.5. The reaction was followed by $C_{18}$ reverse phase HPLC. After 30 min, the derivatized peptide product was separated from the reaction mixture by $C_8$ Sep-Pak solid phase extraction. The bound sample was washed with 2 mL of 10% methaol/$H_2O$ and eluted in 3 1 mL fractions of 60% methanol. This protocol is repeated for the following ubiquitination recognition elements, Arg-εAhx-Lys, Arg-β-Ala-εAhx-Lys, Arg-εAhx-εAhx-Lys, Phe-εAhx-Lys, Phe-β-Ala-εAhx-Lys, Phe-εAhx-εAhx-Lys, KAADADEWCDSGLGSLGPDA (SEQ ID NO 42) where the S in bold are phosphorylated, RHALDDVSNK (SEQ ID NO 54), HGFPPEVEEQDVGTLPISCAQESGMDRHK (SEQ ID NO 55). This generated a series of compounds for testing in the rabbit reticulocyte lysate.

Thioredoxin was prepared following standard method from the plasmid vector pBAD/Thio, (Invitrogen, Carlsbad, Calif.). The plasmid vector was transformed into TOP10 cells and colonies grown up in LB with 50 micrograms/ml ampicillin overnight at 37 C. This overnight culture was then used to inoculate a large culture of LB with 50 micrograms/ml ampicillin and supplemented with arabinose to induce expression. The culture was then harvested and lysed by sonication and run on to a ProBond™ column (Invitrogen), following the manufactures protocol to yield purified thioredoxin.

Thioredoxin was labeled by Lofstrand Laboratories Ltd. (Gaithersburg, Md.) Labeled to 0.12–0.50 μCi/μg by oxidation of $Na^{125}I$ using an iodobead chloramine-T procedure.

The ubiquitin-dependent protein degradation assay was preformed by the addition of 70 μL of rabbit reticulocyte lysate and 5 μL of 0.06 μCi/μL $^{125}$I-labeled thioredoxin to 175 mL of reaction buffer containing 40 mM Tris pH 7.6, 2 mM DTT, 5 mM MgCl$_2$, 0.5 mM ATP, 35 μg creatine phosphokinase (Sigma) and 10 mM phosphocreatine. To demonstrate the targeted degradation of the thioredoxin, various concentrations of the compounds from the above synthesis were added to the lysate (10 to 0.001 mM). The reaction were run at 37 C in a heating block, and at time points 30 μL of the reaction was transferred to 50 μL of cold 100 mg/mL BSA and protein was precipitated by the addition of 420 μL of 23% TCA followed by 15 min on ice. The precipitated samples were microfuged for 2 min at 5000 rpm and 300 μL of supernatant was then counted for TCA-soluble $^{125}$I on a gamma counter (Hidex).

Time points are taken every 30 min from 0 to 120 min. Results demonstrate the targeted degradation.

It will be readily apparent to those skilled in the art that numerous modifications and additions may be made to both the present invention without departing from the invention disclosed.

---

What is claimed is:

1. A method of generating a compound for activating ubiquitination of a target protein which comprises covalently linking a target protein binding element able to bind specifically to said target protein to a ubiquitination recognition element.

* * * * *

SEQUENCE LISTING

<160> NUMBER OF SEQ ID NOS: 67

<210> SEQ ID NO 1
<211> LENGTH: 20
<212> TYPE: PRT
<213> ORGANISM: Unknown Organism
<220> FEATURE:
<223> OTHER INFORMATION: Description of Unknown Organism: PEST example
      sequence

<400> SEQUENCE: 1

Met Glu Phe Met His Ile Ser Pro Pro Glu Pro Glu Ser Glu Glu Glu
 1               5                  10                  15

Glu Glu His Ser
            20

<210> SEQ ID NO 2
<211> LENGTH: 10
<212> TYPE: PRT
<213> ORGANISM: Unknown Organism
<220> FEATURE:
<223> OTHER INFORMATION: Description of Unknown Organism: PEST example
      sequence

<400> SEQUENCE: 2

Met Glu Phe Met His Glu Ser His Ser Ser
 1               5                  10

<210> SEQ ID NO 3
<211> LENGTH: 16
<212> TYPE: PRT
<213> ORGANISM: Unknown Organism
<220> FEATURE:
<223> OTHER INFORMATION: Description of Unknown Organism: PEST example
      sequence

<400> SEQUENCE: 3

Met Glu Phe Met His Ile Ser Pro Pro Glu Pro Glu Ser His Ser Ser
 1               5                  10                  15

<210> SEQ ID NO 4
<211> LENGTH: 15
<212> TYPE: PRT
<213> ORGANISM: Unknown Organism
<220> FEATURE:
<223> OTHER INFORMATION: Description of Unknown Organism: PEST example
      sequence

<400> SEQUENCE: 4

Met Glu Phe Met His Glu Ser Glu Glu Glu Glu Glu His Ser Ser
 1               5                  10                  15

```
<210> SEQ ID NO 5
<211> LENGTH: 10
<212> TYPE: PRT
<213> ORGANISM: Unknown Organism
<220> FEATURE:
<223> OTHER INFORMATION: Description of Unknown Organism: PEST example
      sequence

<400> SEQUENCE: 5

Met Glu Ala Ser Glu Glu Glu Glu Glu Phe
 1               5                  10

<210> SEQ ID NO 6
<211> LENGTH: 28
<212> TYPE: PRT
<213> ORGANISM: Unknown Organism
<220> FEATURE:
<223> OTHER INFORMATION: Description of Unknown Organism: PEST example
      sequence

<400> SEQUENCE: 6

His Gly Phe Pro Pro Glu Val Glu Glu Gln Asp Asp Gly Thr Leu Pro
 1               5                  10                  15

Met Ser Cys Ala Gln Glu Ser Gly Met Asp Arg His
             20                  25

<210> SEQ ID NO 7
<211> LENGTH: 28
<212> TYPE: PRT
<213> ORGANISM: Unknown Organism
<220> FEATURE:
<223> OTHER INFORMATION: Description of Unknown Organism: PEST example
      sequence

<400> SEQUENCE: 7

His Gly Phe Pro Pro Ala Val Ala Ala Gln Asp Asp Gly Thr Leu Pro
 1               5                  10                  15

Met Ser Cys Ala Gln Glu Ser Gly Met Asp Arg His
             20                  25

<210> SEQ ID NO 8
<211> LENGTH: 28
<212> TYPE: PRT
<213> ORGANISM: Unknown Organism
<220> FEATURE:
<223> OTHER INFORMATION: Description of Unknown Organism: PEST example
      sequence

<400> SEQUENCE: 8

His Gly Phe Pro Pro Glu Val Glu Glu Gln Asp Asp Gly Ala Leu Pro
 1               5                  10                  15

Met Ser Cys Ala Gln Glu Ser Gly Met Asp Arg His
             20                  25

<210> SEQ ID NO 9
<211> LENGTH: 28
<212> TYPE: PRT
<213> ORGANISM: Unknown Organism
<220> FEATURE:
<223> OTHER INFORMATION: Description of Unknown Organism: PEST example
      sequence

<400> SEQUENCE: 9

His Gly Phe Pro Pro Glu Val Glu Glu Gln Asp Asp Gly Thr Leu Pro
 1               5                  10                  15

Met Ser Cys Ala Gln Glu Ser Gly Met Asp His His
```

20              25

<210> SEQ ID NO 10
<211> LENGTH: 28
<212> TYPE: PRT
<213> ORGANISM: Unknown Organism
<220> FEATURE:
<223> OTHER INFORMATION: Description of Unknown Organism: PEST example
      sequence

<400> SEQUENCE: 10

His Gly Phe Pro Pro Glu Val Glu Glu Gln Asp Val Gly Thr Leu Pro
 1               5                  10                  15

Met Ser Cys Ala Gln Glu Ser Gly Met Asp Arg His
            20                  25

<210> SEQ ID NO 11
<211> LENGTH: 28
<212> TYPE: PRT
<213> ORGANISM: Unknown Organism
<220> FEATURE:
<223> OTHER INFORMATION: Description of Unknown Organism: PEST example
      sequence

<400> SEQUENCE: 11

His Gly Phe Pro Pro Glu Val Glu Glu Gln Asp Val Gly Thr Leu Pro
 1               5                  10                  15

Ile Ser Cys Ala Gln Glu Ser Gly Met Asp Arg His
            20                  25

<210> SEQ ID NO 12
<211> LENGTH: 28
<212> TYPE: PRT
<213> ORGANISM: Unknown Organism
<220> FEATURE:
<223> OTHER INFORMATION: Description of Unknown Organism: PEST example
      sequence

<400> SEQUENCE: 12

His Gly Phe Pro Pro Glu Val Glu Glu Gln Asp Ala Ser Thr Leu Pro
 1               5                  10                  15

Val Ser Cys Ala Trp Glu Ser Gly Met Lys Arg His
            20                  25

<210> SEQ ID NO 13
<211> LENGTH: 26
<212> TYPE: PRT
<213> ORGANISM: Unknown Organism
<220> FEATURE:
<223> OTHER INFORMATION: Description of Unknown Organism: PEST example
      sequence

<400> SEQUENCE: 13

Phe Pro Pro Gly Val Glu Glu Pro Asp Val Gly Pro Leu Pro Val Ser
 1               5                  10                  15

Cys Ala Trp Glu Ser Gly Met Lys Arg His
            20                  25

<210> SEQ ID NO 14
<211> LENGTH: 27
<212> TYPE: PRT
<213> ORGANISM: Unknown Organism
<220> FEATURE:
<223> OTHER INFORMATION: Description of Unknown Organism: PEST example
      sequence

```
<400> SEQUENCE: 14

Phe Leu Ala Glu Val Glu Glu Gln Asp Val Ala Ser Leu Pro Leu Ser
 1               5                  10                  15

Cys Ala Cys Glu Ser Gly Ile Glu Tyr Pro Ala
            20                  25

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: MOD_RES
<222> LOCATION: (2)..(3)
<223> OTHER INFORMATION: any amino acid
<220> FEATURE:
<221> NAME/KEY: MOD_RES
<222> LOCATION: (10)..(12)
<223> OTHER INFORMATION: any amino acid
<220> FEATURE:
<221> NAME/KEY: MOD_RES
<222> LOCATION: (15)
<223> OTHER INFORMATION: any amino acid
<220> FEATURE:
<221> NAME/KEY: MOD_RES
<222> LOCATION: (19)
<223> OTHER INFORMATION: any amino acid
<220> FEATURE:
<221> NAME/KEY: MOD_RES
<222> LOCATION: (23)..(24)
<223> OTHER INFORMATION: any amino acid
<220> FEATURE:
<221> NAME/KEY: MOD_RES
<222> LOCATION: (25)
<223> OTHER INFORMATION: optional amino acid

<400> SEQUENCE: 15

Phe Xaa Xaa Glu Val Glu Glu Gln Asp Xaa Xaa Xaa Leu Pro Xaa Ser
 1               5                  10                  15

Cys Ala Xaa Glu Ser Gly Xaa Xaa Xaa
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: MOD_RES
<222> LOCATION: (2)..(3)
<223> OTHER INFORMATION: any amino acid
<220> FEATURE:
<221> NAME/KEY: MOD_RES
<222> LOCATION: (10)..(12)
<223> OTHER INFORMATION: any amino acid
<220> FEATURE:
<221> NAME/KEY: MOD_RES
<222> LOCATION: (15)
<223> OTHER INFORMATION: any amino acid
<220> FEATURE:
<221> NAME/KEY: MOD_RES
<222> LOCATION: (19)
<223> OTHER INFORMATION: any amino acid
<220> FEATURE:
<221> NAME/KEY: MOD_RES
<222> LOCATION: (23)..(24)
<223> OTHER INFORMATION: any amino acid
<220> FEATURE:
<221> NAME/KEY: MOD_RES
```

```
<222> LOCATION: (25)
<223> OTHER INFORMATION: optional amino acid
<220> FEATURE:
<221> NAME/KEY: MOD_RES
<222> LOCATION: (26)
<223> OTHER INFORMATION: any amino acid

<400> SEQUENCE: 16

Phe Xaa Xaa Ala Val Ala Ala Gln Asp Xaa Xaa Xaa Leu Pro Xaa Ser
 1               5                  10                  15

Cys Ala Xaa Glu Ser Gly Xaa Xaa Xaa Xaa
            20                  25

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: MOD_RES
<222> LOCATION: (3)..(4)
<223> OTHER INFORMATION: any amino acid
<220> FEATURE:
<221> NAME/KEY: MOD_RES
<222> LOCATION: (8)
<223> OTHER INFORMATION: any amino acid
<220> FEATURE:
<221> NAME/KEY: MOD_RES
<222> LOCATION: (9)..(10)
<223> OTHER INFORMATION: optional amino acid
<220> FEATURE:
<221> NAME/KEY: MOD_RES
<222> LOCATION: (12)..(14)
<223> OTHER INFORMATION: any amino acid
<220> FEATURE:
<221> NAME/KEY: MOD_RES
<222> LOCATION: (16)..(17)
<223> OTHER INFORMATION: any amino acid
<220> FEATURE:
<221> NAME/KEY: MOD_RES
<222> LOCATION: (26)..(28)
<223> OTHER INFORMATION: any amino acid

<400> SEQUENCE: 17

His Gly Xaa Xaa Pro Glu Val Xaa Xaa Xaa Asp Xaa Xaa Xaa Leu Xaa
 1               5                  10                  15

Xaa Ser Cys Ala Gln Glu Ser Gly Met Xaa Xaa Xaa
            20                  25

<210> SEQ ID NO 18
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 18

Arg His Ala Leu Asp Asp Val Ser Asn
 1               5

<210> SEQ ID NO 19
<211> LENGTH: 9
<212> TYPE: PRT
<213> ORGANISM: Unknown Organism
<220> FEATURE:
<223> OTHER INFORMATION: Description of Unknown Organism: D box example
      sequence
```

```
<400> SEQUENCE: 19

Arg Leu Ala Leu Asn Asn Val Thr Asn
  1               5

<210> SEQ ID NO 20
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 20

Arg Ala Ala Leu Gly Asp Val Ser Asn
  1               5

<210> SEQ ID NO 21
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 21

Arg Gln Val Leu Gly Asp Ile Gly Asn
  1               5

<210> SEQ ID NO 22
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 22

Arg Ala Ala Leu Gly Asp Leu Gln Asn
  1               5

<210> SEQ ID NO 23
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 23

Arg Ala Ala Leu Gly Asn Ile Ser Asn
  1               5

<210> SEQ ID NO 24
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 24

Arg Asn Thr Leu Gly Asp Ile Gly Asn
  1               5

<210> SEQ ID NO 25
<211> LENGTH: 9
<212> TYPE: PRT
```

```
<213> ORGANISM: Unknown Organism
<220> FEATURE:
<223> OTHER INFORMATION: Description of Unknown Organism: D box example
      sequence

<400> SEQUENCE: 25

Arg Thr Ala Leu Gly Asp Ile Gly Asn
  1               5

<210> SEQ ID NO 26
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 26

Arg Ala Ala Leu Gly Glu Ile Gly Asn
  1               5

<210> SEQ ID NO 27
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 27

Arg Ala Val Leu Glu Glu Ile Gly Asn
  1               5

<210> SEQ ID NO 28
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 28

Arg Ser Ala Phe Gly Asp Ile Thr Asn
  1               5

<210> SEQ ID NO 29
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 29

Arg Ser Ile Leu Gly Val Ile Gln Ser
  1               5

<210> SEQ ID NO 30
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 30

Arg Ala Ala Leu Gly Val Ile Thr Asn
  1               5
```

```
<210> SEQ ID NO 31
<211> LENGTH: 10
<212> TYPE: PRT
<213> ORGANISM: Unknown Organism
<220> FEATURE:
<223> OTHER INFORMATION: Description of Unknown Organism: D box example
      sequence

<400> SEQUENCE: 31

Arg Thr Val Leu Gly Val Ile Gly Asp Asn
  1               5                  10

<210> SEQ ID NO 32
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 32

Arg Thr Val Gly Val Leu Gln Glu Asn
  1               5

<210> SEQ ID NO 33
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 33

Arg Ala Ala Leu Gly Thr Val Gly Glu
  1               5

<210> SEQ ID NO 34
<211> LENGTH: 10
<212> TYPE: PRT
<213> ORGANISM: Unknown Organism
<220> FEATURE:
<223> OTHER INFORMATION: Description of Unknown Organism: D box example
      sequence

<400> SEQUENCE: 34

Arg Thr Val Leu Gly Val Leu Thr Glu Asn
  1               5                  10

<210> SEQ ID NO 35
<211> LENGTH: 11
<212> TYPE: PRT
<213> ORGANISM: Unknown Organism
<220> FEATURE:
<223> OTHER INFORMATION: Description of Unknown Organism: D box example
      sequence

<400> SEQUENCE: 35

Arg Ala Ala Leu Ala Val Leu Lys Ser Gly Asn
  1               5                  10

<210> SEQ ID NO 36
<211> LENGTH: 9
<212> TYPE: PRT
<213> ORGANISM: Unknown Organism
<220> FEATURE:
<223> OTHER INFORMATION: Description of Unknown Organism: D box example
      sequence
```

```
<400> SEQUENCE: 36

Arg Leu Pro Leu Ala Ala Lys Asp Asn
  1               5

<210> SEQ ID NO 37
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 37

Arg Gln Leu Phe Pro Ile Pro Leu Asn
  1               5

<210> SEQ ID NO 38
<211> LENGTH: 9
<212> TYPE: PRT
<213> ORGANISM: Unknown Organism
<220> FEATURE:
<223> OTHER INFORMATION: Description of Unknown Organism: D box example
      sequence

<400> SEQUENCE: 38

Arg Arg Thr Leu Lys Val Ile Gln Pro
  1               5

<210> SEQ ID NO 39
<211> LENGTH: 9
<212> TYPE: PRT
<213> ORGANISM: Unknown Organism
<220> FEATURE:
<223> OTHER INFORMATION: Description of Unknown Organism: D box general
      structure
<220> FEATURE:
<221> NAME/KEY: MOD_RES
<222> LOCATION: (2)
<223> OTHER INFORMATION: Ala or Thr
<220> FEATURE:
<221> NAME/KEY: MOD_RES
<222> LOCATION: (3)
<223> OTHER INFORMATION: amino acid present more than %50 of the time
<220> FEATURE:
<221> NAME/KEY: MOD_RES
<222> LOCATION: (6)
<223> OTHER INFORMATION: any amino acid
<220> FEATURE:
<221> NAME/KEY: MOD_RES
<222> LOCATION: (7)
<223> OTHER INFORMATION: Ile or Val
<220> FEATURE:
<221> NAME/KEY: MOD_RES
<222> LOCATION: (8)
<223> OTHER INFORMATION: Gly or Thr
<220> FEATURE:
<221> NAME/KEY: MOD_RES
<222> LOCATION: (9)
<223> OTHER INFORMATION: amino acid present more than %50 of the time

<400> SEQUENCE: 39

Arg Xaa Ala Leu Gly Xaa Xaa Xaa Asn
  1               5

<210> SEQ ID NO 40
<211> LENGTH: 21
<212> TYPE: PRT
<213> ORGANISM: Unknown Organism
<220> FEATURE:
<223> OTHER INFORMATION: Description of Unknown Organism: ubiquitination
```

```
                             recognition element

<400> SEQUENCE: 40

Lys Glu Phe Ala Val Pro Asn Glu Thr Ser Asp Ser Gly Phe Ile Ser
 1               5                  10                  15

Gly Pro Gln Ser Ser
            20

<210> SEQ ID NO 41
<211> LENGTH: 22
<212> TYPE: PRT
<213> ORGANISM: Unknown Organism
<220> FEATURE:
<223> OTHER INFORMATION: Description of Unknown Organism: ubiquitination
      recognition element

<400> SEQUENCE: 41

Lys Gly Pro Asp Glu Ala Glu Glu Ser Gln Tyr Asp Ser Gly Leu Glu
 1               5                  10                  15

Ser Leu Arg Ser Leu Arg
            20

<210> SEQ ID NO 42
<211> LENGTH: 20
<212> TYPE: PRT
<213> ORGANISM: Unknown Organism
<220> FEATURE:
<223> OTHER INFORMATION: Description of Unknown Organism: ubiquitination
      recognition element

<400> SEQUENCE: 42

Lys Ala Ala Asp Ala Asp Glu Trp Cys Asp Ser Gly Leu Gly Ser Leu
 1               5                  10                  15

Gly Pro Asp Ala
            20

<210> SEQ ID NO 43
<211> LENGTH: 21
<212> TYPE: PRT
<213> ORGANISM: Unknown Organism
<220> FEATURE:
<223> OTHER INFORMATION: Description of Unknown Organism: ubiquitination
      recognition element

<400> SEQUENCE: 43

Lys Lys Glu Arg Leu Leu Asp Asp Arg His Asp Ser Gly Leu Asp Ser
 1               5                  10                  15

Met Lys Asp Glu Glu
            20

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: MOD_RES
<222> LOCATION: (2)...(11)
<223> OTHER INFORMATION: any amino acid
<220> FEATURE:
<223> OTHER INFORMATION: positions 2-11 may encompass X(8-10)

<400> SEQUENCE: 44

Lys Xaa Xaa Xaa Xaa Xaa Xaa Xaa Xaa Xaa Xaa Asp Ser Gly
```

```
<210> SEQ ID NO 45
<211> LENGTH: 12
<212> TYPE: PRT
<213> ORGANISM: Unknown Organism
<220> FEATURE:
<223> OTHER INFORMATION: Description of Unknown Organism: ubiqitination
      recognition element

<400> SEQUENCE: 45

Ser Tyr Leu Asp Ser Gly Ile His Ser Gly Ala Thr
 1               5                  10

<210> SEQ ID NO 46
<211> LENGTH: 12
<212> TYPE: PRT
<213> ORGANISM: Unknown Organism
<220> FEATURE:
<223> OTHER INFORMATION: Description of Unknown Organism: ubiqitination
      recognition element

<400> SEQUENCE: 46

Arg Ala Glu Asp Ser Gly Asn Glu Ser Glu Gly Glu
 1               5                  10

<210> SEQ ID NO 47
<211> LENGTH: 6
<212> TYPE: PRT
<213> ORGANISM: Unknown Organism
<220> FEATURE:
<223> OTHER INFORMATION: Description of Unknown Organism: example
      peptide
<220> FEATURE:
<221> NAME/KEY: MOD_RES
<222> LOCATION: (3)...(4)
<223> OTHER INFORMATION: any amino acid

<400> SEQUENCE: 47

Cys Cys Xaa Xaa Cys Cys
 1               5

<210> SEQ ID NO 48
<211> LENGTH: 17
<212> TYPE: PRT
<213> ORGANISM: Unknown Organism
<220> FEATURE:
<223> OTHER INFORMATION: Description of Unknown Organism: example
      peptide

<400> SEQUENCE: 48

Trp Glu Ala Ala Ala Arg Glu Ala Cys Cys Arg Glu Cys Cys Ala Arg
 1               5                  10                  15

Ala

<210> SEQ ID NO 49
<211> LENGTH: 17
<212> TYPE: PRT
<213> ORGANISM: Unknown Organism
<220> FEATURE:
<223> OTHER INFORMATION: Description of Unknown Organism: example
      peptide

<400> SEQUENCE: 49

Ala Glu Ala Ala Ala Arg Glu Ala Cys Cys Arg Glu Cys Cys Ala Arg
 1               5                  10                  15

Ala
```

```
<210> SEQ ID NO 50
<211> LENGTH: 22
<212> TYPE: PRT
<213> ORGANISM: Unknown Organism
<220> FEATURE:
<223> OTHER INFORMATION: Description of Unknown Organism: ubiquitination
      recognition element

<400> SEQUENCE: 50

Lys Lys Glu Arg Leu Leu Asp Asp Arg His Asp Ser Gly Leu Asp Ser
 1               5                  10                  15

Met Lys Asp Glu Glu Cys
            20

<210> SEQ ID NO 51
<211> LENGTH: 12
<212> TYPE: PRT
<213> ORGANISM: Unknown Organism
<220> FEATURE:
<223> OTHER INFORMATION: Description of Unknown Organism: ubiquitination
      recognition element

<400> SEQUENCE: 51

Arg Ala Ala Leu Ala Val Leu Lys Ser Gly Asn Cys
 1               5                  10

<210> SEQ ID NO 52
<211> LENGTH: 29
<212> TYPE: PRT
<213> ORGANISM: Unknown Organism
<220> FEATURE:
<223> OTHER INFORMATION: Description of Unknown Organism: ubiquitination
      recognition element

<400> SEQUENCE: 52

His Gly Phe Pro Pro Glu Val Glu Glu Gln Asp Val Gly Thr Leu Pro
 1               5                  10                  15

Ile Ser Cys Ala Gln Glu Ser Gly Met Asp Arg His Cys
            20                  25

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: consensus
      sequence
<220> FEATURE:
<221> NAME/KEY: MOD_RES
<222> LOCATION: (2)...(3)
<223> OTHER INFORMATION: any amino acid
<220> FEATURE:
<221> NAME/KEY: MOD_RES
<222> LOCATION: (6)
<223> OTHER INFORMATION: any amino acid
<220> FEATURE:
<221> NAME/KEY: MOD_RES
<222> LOCATION: (8)
<223> OTHER INFORMATION: any amino acid

<400> SEQUENCE: 53

Arg Xaa Xaa Leu Gly Xaa Ile Xaa Asn
 1               5

<210> SEQ ID NO 54
<211> LENGTH: 10
<212> TYPE: PRT
```

```
<213> ORGANISM: Unknown Organism
<220> FEATURE:
<223> OTHER INFORMATION: Description of Unknown Organism: ubiquitination
      recognition element

<400> SEQUENCE: 54

Arg His Ala Leu Asp Asp Val Ser Asn Lys
 1               5                  10

<210> SEQ ID NO 55
<211> LENGTH: 29
<212> TYPE: PRT
<213> ORGANISM: Unknown Organism
<220> FEATURE:
<223> OTHER INFORMATION: Description of Unknown Organism: ubiquitination
      recognition element

<400> SEQUENCE: 55

His Gly Phe Pro Pro Glu Val Glu Glu Gln Asp Val Gly Thr Leu Pro
 1               5                  10                  15

Ile Ser Cys Ala Gln Glu Ser Gly Met Asp Arg His Lys
             20                  25

<210> SEQ ID NO 56
<211> LENGTH: 4
<212> TYPE: PRT
<213> ORGANISM: Unknown Organism
<220> FEATURE:
<223> OTHER INFORMATION: Description of Unknown Organism: binding
      peptide

<400> SEQUENCE: 56

Tyr Glu Glu Ile
 1

<210> SEQ ID NO 57
<211> LENGTH: 18
<212> TYPE: PRT
<213> ORGANISM: Unknown Organism
<220> FEATURE:
<223> OTHER INFORMATION: Description of Unknown Organism: binding
      peptide

<400> SEQUENCE: 57

Asp Arg Glu Gly Cys Arg Arg Gly Trp Val Gly Gln Cys Lys Ala Trp
 1               5                  10                  15

Phe Asn

<210> SEQ ID NO 58
<211> LENGTH: 22
<212> TYPE: PRT
<213> ORGANISM: Unknown Organism
<220> FEATURE:
<223> OTHER INFORMATION: Description of Unknown Organism: binding
      peptide

<400> SEQUENCE: 58

Glu Thr Pro Thr Phe Thr Trp Glu Glu Ser Asn Ala Tyr Tyr Trp Gln
 1               5                  10                  15

Pro Tyr Ala Leu Pro Leu
             20

<210> SEQ ID NO 59
<211> LENGTH: 12
<212> TYPE: PRT
<213> ORGANISM: Unknown Organism
```

```
<220> FEATURE:
<223> OTHER INFORMATION: Description of Unknown Organism: binding
      peptide

<400> SEQUENCE: 59

Thr Phe Val Tyr Trp Gln Pro Tyr Ala Leu Pro Leu
 1               5                  10

<210> SEQ ID NO 60
<211> LENGTH: 15
<212> TYPE: PRT
<213> ORGANISM: Unknown Organism
<220> FEATURE:
<223> OTHER INFORMATION: Description of Unknown Organism: binding
      peptide

<400> SEQUENCE: 60

Val Ser Leu Ala Arg Arg Pro Leu Pro Pro Leu Pro Gly Gly Lys
 1               5                  10                  15

<210> SEQ ID NO 61
<211> LENGTH: 17
<212> TYPE: PRT
<213> ORGANISM: Unknown Organism
<220> FEATURE:
<223> OTHER INFORMATION: Description of Unknown Organism: binding
      peptide

<400> SEQUENCE: 61

Lys Gly Gly Gly Ala Ala Pro Pro Leu Pro Pro Arg Asn Arg Pro Arg
 1               5                  10                  15

Leu

<210> SEQ ID NO 62
<211> LENGTH: 15
<212> TYPE: PRT
<213> ORGANISM: Unknown Organism
<220> FEATURE:
<223> OTHER INFORMATION: Description of Unknown Organism: binding
      peptide

<400> SEQUENCE: 62

Ala Glu Cys His Pro Gln Gly Pro Pro Cys Ile Glu Gly Arg Lys
 1               5                  10                  15

<210> SEQ ID NO 63
<211> LENGTH: 13
<212> TYPE: PRT
<213> ORGANISM: Unknown Organism
<220> FEATURE:
<223> OTHER INFORMATION: Description of Unknown Organism: binding
      peptide

<400> SEQUENCE: 63

Gly Ala Cys Arg Arg Glu Thr Ala Trp Ala Cys Gly Ala
 1               5                  10

<210> SEQ ID NO 64
<211> LENGTH: 12
<212> TYPE: PRT
<213> ORGANISM: Unknown Organism
<220> FEATURE:
<223> OTHER INFORMATION: Description of Unknown Organism: binding
      peptide

<400> SEQUENCE: 64

Asp Ile Thr Trp Asp Gln Leu Trp Asp Leu Met Lys
```

```
1               5              10
```

```
<210> SEQ ID NO 65
<211> LENGTH: 13
<212> TYPE: PRT
<213> ORGANISM: Unknown Organism
<220> FEATURE:
<223> OTHER INFORMATION: Description of Unknown Organism: binding
      peptide

<400> SEQUENCE: 65

Arg Asn Met Ser Trp Leu Glu Leu Trp Glu His Met Lys
 1               5                  10

<210> SEQ ID NO 66
<211> LENGTH: 4
<212> TYPE: PRT
<213> ORGANISM: Unknown Organism
<220> FEATURE:
<223> OTHER INFORMATION: Description of Unknown Organism: ubiquitination
      recognition element
<220> FEATURE:
<221> NAME/KEY: MOD_RES
<222> LOCATION: (3)
<223> OTHER INFORMATION: beta-Ala
<220> FEATURE:
<223> OTHER INFORMATION: caproic acid linker between positions 3-4

<400> SEQUENCE: 66

Arg Ala Ala Cys
 1

<210> SEQ ID NO 67
<211> LENGTH: 4
<212> TYPE: PRT
<213> ORGANISM: Unknown Organism
<220> FEATURE:
<223> OTHER INFORMATION: Description of Unknown Organism: ubiquitination
      recognition element
<220> FEATURE:
<221> NAME/KEY: MOD_RES
<222> LOCATION: (3)
<223> OTHER INFORMATION: beta-Ala
<220> FEATURE:
<223> OTHER INFORMATION: caproic acid linker between positions 3-4

<400> SEQUENCE: 67

Pro Ala Ala Cys
```